(12) United States Patent
Kroll

(10) Patent No.: US 7,305,266 B1
(45) Date of Patent: Dec. 4, 2007

(54) CARDIAC STIMULATION DEVICES AND METHODS FOR MEASURING IMPEDANCES ASSOCIATED WITH THE HEART

(75) Inventor: Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 561 days.

(21) Appl. No.: 10/881,676

(22) Filed: Jun. 29, 2004

Related U.S. Application Data

(63) Continuation-in-part of application No. 09/858,183, filed on May 14, 2001, now abandoned.

(51) Int. Cl.
*A61N 1/368* (2006.01)

(52) U.S. Cl. .......................................... 607/28; 607/24

(58) Field of Classification Search ................ 600/547; 607/28, 8, 20, 24
See application file for complete search history.

(56) References Cited

U.S. PATENT DOCUMENTS

| | | | |
|---|---|---|---|
| 4,674,518 A | 6/1987 | Salo | |
| 5,154,171 A | 10/1992 | Chirife | |
| 5,314,449 A | 5/1994 | Lindgren | |
| 5,417,717 A | 5/1995 | Salo et al. | 607/18 |
| 5,466,254 A | 11/1995 | Helland | 607/123 |
| 5,501,702 A | 3/1996 | Plicchi et al. | |
| 5,626,624 A | 5/1997 | Schaldach et al. | |
| 5,782,774 A | 7/1998 | Shmulewitz | 600/547 |
| 6,070,100 A | 5/2000 | Bakels et al. | |
| 6,095,987 A | 8/2000 | Shmulewitz et al. | 600/547 |
| 6,223,082 B1 | 4/2001 | Bakels et al. | 607/17 |
| 6,278,894 B1 | 8/2001 | Salo et al. | 600/547 |
| 6,405,087 B1 | 6/2002 | Snell | |
| 6,473,648 B1 | 10/2002 | Prutchi et al. | |
| 6,647,292 B1 | 11/2003 | Bardy et al. | 607/5 |
| 6,754,530 B2 * | 6/2004 | Bakels et al. | 607/14 |

FOREIGN PATENT DOCUMENTS

| | | |
|---|---|---|
| EP | 0904012 B1 | 4/1997 |
| EP | 0 990 451 | 4/2000 |
| WO | WO 97/38628 | 10/1997 |
| WO | 99/30777 | 6/1999 |
| WO | 00/78391 | 12/2000 |
| WO | 00/78391 A1 | 12/2000 |

* cited by examiner

*Primary Examiner*—George R. Evanisko

(57) ABSTRACT

An exemplary method includes introducing current between a first pair of electrodes configured for placement internally in a patient, triggering a potential measurement between a second pair of electrodes configured for placement internally in a patient wherein communication of a signal through the patient allows for proper triggering, measuring potential between the second pair of electrodes and, based at least in part on the measuring and the introducing, determining a cardiac condition. Other exemplary methods, devices, systems, etc., are also disclosed.

10 Claims, 26 Drawing Sheets

EXEMPLARY ARRANGEMENT

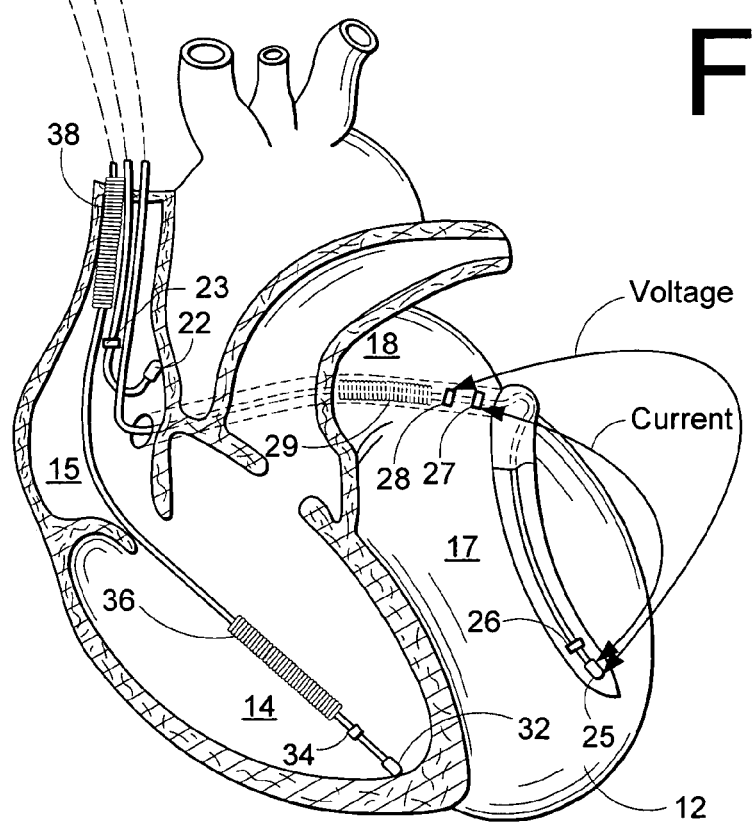
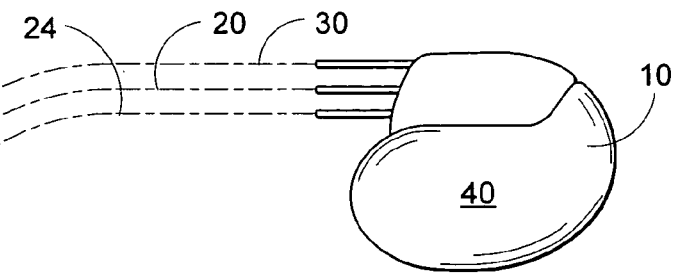
Fig. 11

… (continued)

CARDIAC STIMULATION DEVICES AND METHODS FOR MEASURING IMPEDANCES ASSOCIATED WITH THE HEART

RELATED APPLICATION

This application is a continuation-in-part of U.S. patent application Ser. No. 09/858,183, filed May 14, 2001, now abandoned titled "Cardiac Stimulation Devices and Methods for Measuring Impedances Associated with the Left Side of the Heart."

TECHNICAL FIELD

The present invention generally relates to cardiac rhythm management devices, such as implantable cardioverter-defibrillators (ICDs) and pacemakers, or combinations thereof. The present invention more particularly relates to such devices which utilize one or more electrodes implanted for introducing current and/or measuring physiological parameters based on measured electrical impedances.

BACKGROUND

Cardiac rhythm management devices, including implantable devices, are well known in the art. Such devices may include, for example, implantable cardiac pacemakers, cardioverters or defibrillators. The devices are generally implanted in an upper portion of the chest, in either the left or right side depending on the type of the device, beneath the skin of a patient within what is known as a subcutaneous pocket. The implantable devices generally function in association with one or more electrode-carrying leads which are implanted within the heart. The electrodes are typically positioned within the right side of the heart, either the right ventricle or right atrium, or both, for making electrical contact with their designated heart chamber. Conductors within the leads couple the electrodes to the device to enable the device to deliver the desired stimulation therapy.

Traditionally, therapy delivery has been limited to the right side of the heart. The reason for this is that implanted electrodes can cause blood clot formation in some patients. If a blood clot were released from the left-side of the heart, as from the left ventricle, it could pass directly to the brain resulting in a paralyzing or fatal stroke. However, a blood clot released from the right side of the heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy from or to the left-side of the heart. These lead structures and methods avoid electrode placement within the left atrium and left ventricle of the heart by lead implantation within the coronary sinus and/or the great vein of the heart which communicates with the coronary sinus and extends down towards the apex of the heart. As is well known, the coronary sinus passes closely adjacent the left atrium and extends into the great vein adjacent the left ventricular free wall. The great vein then continues adjacent the left ventricle towards the apex of the heart.

It has been observed that electrodes placed in the coronary sinus and great vein may be used for left atrial pacing, left ventricular pacing, and even cardioversion and defibrillation. This work is being done to address the needs of a patient population with left ventricular dysfunction and congestive heart failure. This patient class has been targeted to receive pacing leads intended for left ventricular pacing, either alone or in conjunction with right ventricular pacing. When delivering such therapy to these patients, it would be desirable to provide device-based measurements of left ventricular function for both monitoring and therapy delivery.

It is known in the art that device-based impedance measurements offer one method for assessing patient condition. It is also well known, however, that bio-impedance measurements can be confounded by signals not directly related to the desired physiology to be measured. For example, a measurement of impedance from a unipolar tip electrode in the right ventricular apex will contain signal components related to respiration, and right ventricular, left ventricular, and aortic hemodynamics. Filtering of the signal can help to isolate the various desired signals, but the filtering required to accurately isolate the desired signals are often not feasible in an implantable cardiac rhythm management device.

It is also known that localization of the desired signals is improved by making proper choice of electrode configurations between which impedance measurements are made. For example, a transchamber impedance technique is known wherein impedance measurements are made between electrodes in the right atrium and right ventricle to assist in isolating the right ventricular hemodynamics.

The advent of cardiac leads for delivering therapy to the left-side of the heart which are often placed in the coronary sinus and great cardiac vein require new techniques for measurement of functional parameters of, or associated with, a heart.

SUMMARY

An exemplary method includes introducing current between a first pair of electrodes configured for placement internally in a patient, triggering a potential measurement between a second pair of electrodes configured for placement internally in a patient wherein communication of a signal through the patient allows for proper triggering, measuring potential between the second pair of electrodes and, based at least in part on the measuring and the introducing, determining a cardiac condition. Other exemplary methods, devices, systems, etc., are also disclosed.

BRIEF DESCRIPTION OF THE DRAWINGS

FIG. 11 is a reproduction of the patient's heart shown in FIG. 1 illustrating an electrode configuration that is suitable for use in ascertaining an impedance measure in accordance with one embodiment.

DETAILED DESCRIPTION

The following description is of the best mode presently contemplated. This description is not to be taken in a limiting sense but is made merely for the purpose of describing the general principles of the illustrative embodiments. The scope of the invention should be ascertained with reference to the issued claims. In the description that follows, like numerals or reference designators will be used to refer to like parts or elements throughout.

Exemplary Stimulation Device

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

Figure 1:
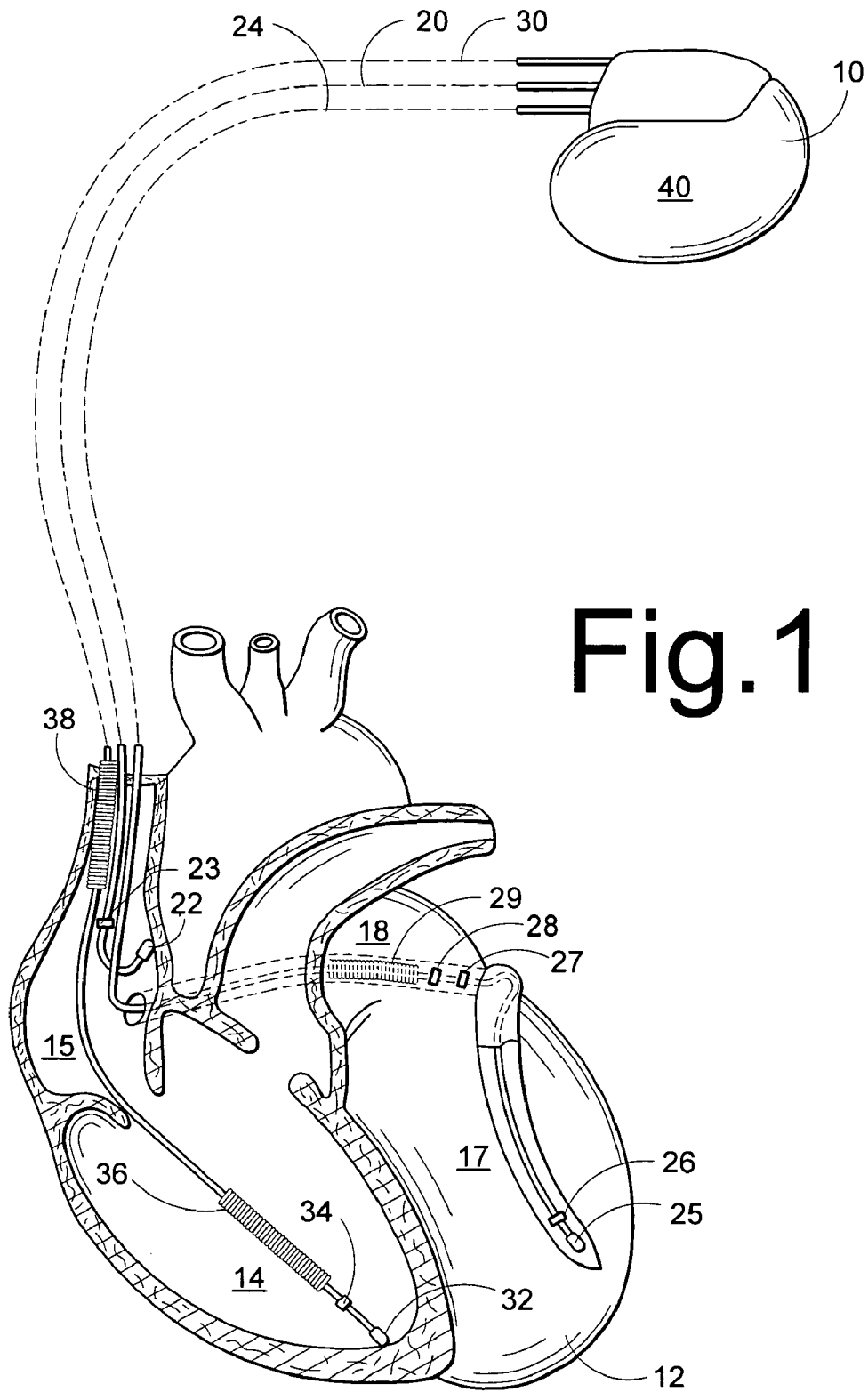
FIG. 1 is a simplified diagram illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 suitable for delivering multi-chamber stimulation and shock therapy. The portions of the heart 10 illustrated include the right ventricle 14, the right atrium 15, the left ventricle 17, and the left atrium 18. As used herein, the left-side of the heart is meant to denote the portions of the heart encompassing the left ventricle 17 and the left atrium 18 and those portions of the coronary sinus, great cardiac vein, and its associated tributaries, which are adjacent the left atrium and left ventricle. As will be seen hereinafter, the device 10 includes a system for measuring a physiological parameter, and more particularly, the left ventricular impedance corresponding to contraction of the heart 12, in accordance with various embodiments described in further detail below.

To sense atrial cardiac signals and to provide right atrial chamber stimulation therapy, the stimulation device 10 is coupled to an implantable right atrial lead 20 having at least an atrial tip electrode 22, and preferably a right atrial ring electrode 23, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place one or more distal electrodes adjacent to the left ventricle 17 and one or more proximal electrodes adjacent to the left atrium 18. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using, for example, a left ventricular tip electrode 25 and a left ventricular ring electrode 26; left atrial pacing therapy using, for example, a first and second left atrial ring electrode, 27 and 28; and shocking therapy using at least a left atrial coil electrode 29. For a complete description of a coronary sinus lead, refer to U.S. Pat. No. 5,466,254, titled "Coronary Sinus Lead with Atrial Sensing Capability" (Helland), which patent is hereby incorporated herein by reference.

The stimulation device 10 is also shown in electrical communication with the patient's heart 12 by way of an implantable right ventricular lead 30 having a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle 14.

Figure 2:
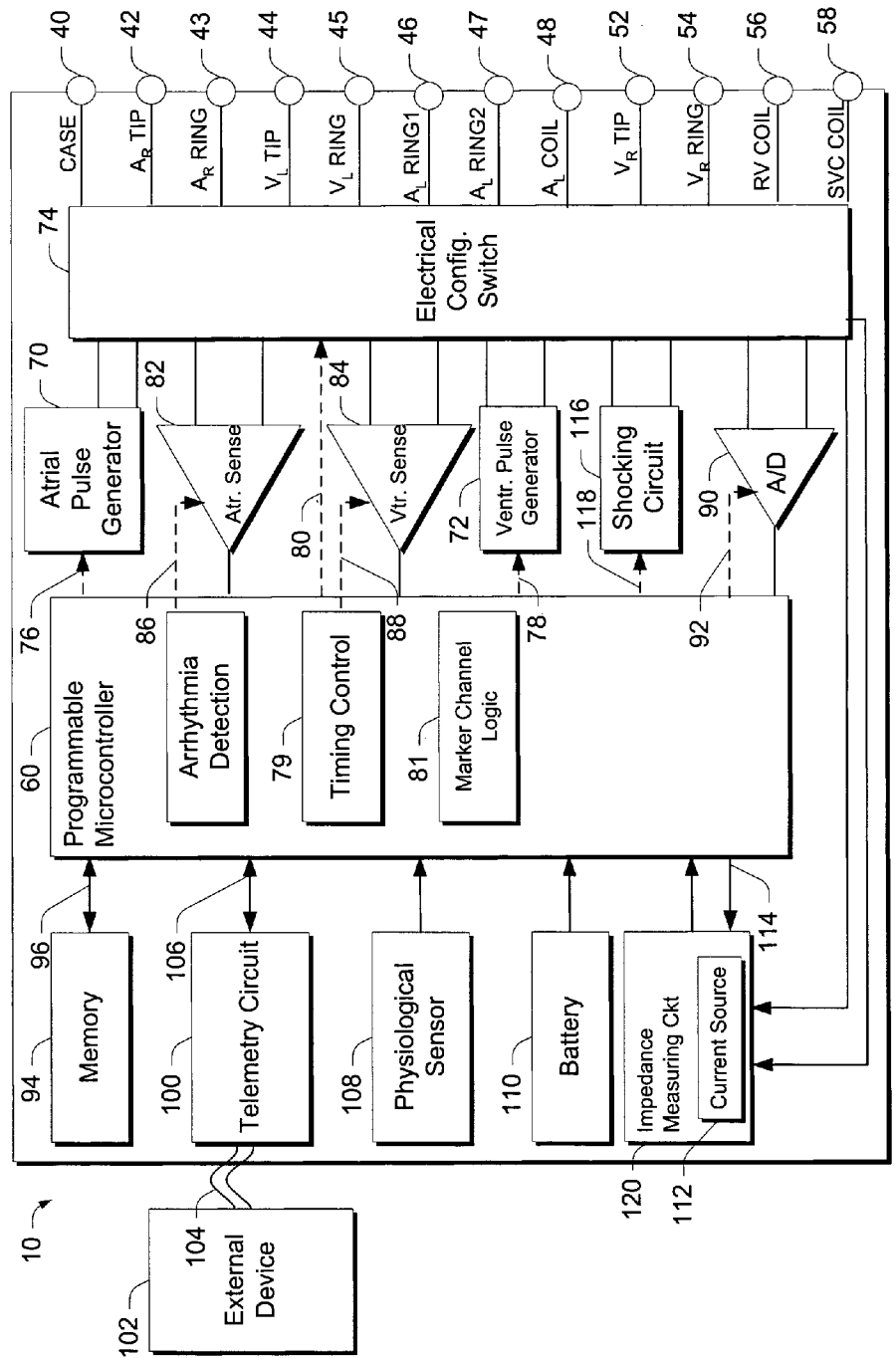
FIG. 2 is a functional block diagram of a multi-chamber implantable stimulation device illustrating exemplary basic elements of a stimulation device which can provide cardioversion, defibrillation and/or pacing stimulation in up to four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation. In addition, it will be appreciated and understood that various processing steps described herein can be implemented in the form of software instructions that are resident on a computer-readable media that is located on the stimulation device. Accordingly, embodiments described herein extend to all forms of computer-readable media, whether on the stimulation device or not, when such media contains instructions that, when executed by one or more processors, implement the methods described herein.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 29, 36, or 38, for shocking purposes.

The housing 40 further includes a connector (not shown) having a plurality of terminals, 42, 43, 44, 45, 46, 47, 48, 52, 54, 56, and 58 (shown schematically and, for convenience, the names of the electrodes to which they are connected are shown next to the terminals). While it is recognized that current devices are limited to the number of terminals due to International Standards, one of skill in the art could readily eliminate some of the terminals/electrodes to fit in the existing device configurations and permit programmability to select which terminals connect to which electrodes. However, in the near future, the standards may change to permit multi-polar in-line connectors, and multiple feedthroughs connectors could readily be manufactured to accommodate the configuration shown in FIG. 2.

As such, to achieve right atrial sensing and pacing, the connector includes at least a right atrial tip terminal 42 and a right atrial ring terminal 43, adapted for connection to the atrial tip electrode and ring electrodes 22 and 23, respectively.

To achieve left chamber sensing, pacing and/or shocking, the connector includes at least a left ventricular tip terminal 44, a left ventricular ring electrode 45, a first left atrial ring terminal 46, a second left atrial ring terminal 47, and a left atrial shocking terminal 48, which are adapted for connection to the left ventricular tip electrode 25, left ventricular ring 26, the first left atrial tip electrode 27, the second left atrial ring electrode 28, and the left atrial coil electrode 29, respectively.

To support right chamber sensing, pacing and/or shocking, the connector further includes a right ventricular tip terminal 52, a right ventricular ring terminal 54, a right ventricular (RV) shocking terminal 56, and an SVC shocking terminal 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller or microprocessor 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing (via marker channel logic 81), etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) and various shocking vectors by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

The atrial sensing circuit 82 or the ventricular sensing circuit 84 preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation. The outputs of the atrial and ventricular sensing circuits, 82 and 84, are connected to the microcontroller 60 for triggering or inhibiting the atrial and ventricular pulse generators, 70 and 72, respectively, in a demand fashion, in response to the absence or presence of cardiac activity, respectively, in the appropriate chambers of the heart.

For arrhythmia detection, the stimulation device 10 utilizes the atrial and ventricular sensing circuits, 82 and 84, to sense cardiac signals for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). A physiological parameter of the heart, which may be measured to optimize such pacing and to indicate when such pacing may be inhibited or terminated is the stroke volume of the heart. Accordingly, the microcontroller 60 responds by adjusting the various pacing parameters (such as rate, AV Delay, A-A Delay, V-V Delay, etc.) at which the atrial and ventricular pulse generators, 70 and 72, generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

It can be a primary function of the stimulation device 10 to operate as an implantable cardioverter/defibrillator (ICD) device. That is, it can detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high (11 to 40 joules) energy, as controlled by the microcontroller 60. Such shocking pulses are applied to the patient's heart through at least two shocking electrodes, and as shown in this embodiment, selected from the left atrial coil electrode 29, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 29 (i.e., using the RV electrode as the common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, the stimulation device 10 is shown as having an impedance measuring circuit 120 including an impedance measuring current source 112 and a voltage measuring circuit 90 (shown in FIG. 2 as an A/D converter), which is enabled by the microcontroller 60 by a control signal 114 for providing stroke volume measurements of the heart. The current source 112 preferably provides an alternating or pulsed excitation current. The voltage measuring circuitry 90 may also take the form of, for example, a differential amplifier.

The uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring a respiration parameter (for example, tidal volume, respiration rate, minute ventilation or volume, abnormal or periodic breathing); measuring thoracic impedance for determining shock thresholds and shock timing (corresponding to the diastolic time); detecting when the device has been implanted; measuring a cardiac parameter (such as, stroke volume, wall thickness, left ventricular volume, etc.); and detecting the opening of the valves, etc. In the present embodiment, the impedance measuring circuit is used to monitor left heart disease and provides appropriate stimulation therapy, such as altering rate, AV, A-A, or V-V delays. The impedance measuring circuit 120 is advantageously coupled to the switch bank 74 so that any desired electrode may be used. Impedance may also be useful in verifying hemodynamic collapse to confirm that ATP has failed and/or VF has begun.

The microcontroller 60 is coupled to the voltage measuring circuit 90 and the current source 112 for receiving a magnitude of the established current and a magnitude of the monitored voltage. The microcontroller 60, operating under program instructions, divides the magnitude of the monitored or measured voltage by the magnitude of the established current to determine an impedance value. Once the impedance signals are determined, they may be delivered to the memory 94 for storage and later retrieved by the microcontroller 60 for therapy adjustment or telemetry transmission. The telemetry circuitry receives the impedance values from the microcontroller 60 and transmits them to the external programmer. The impedance value may then be monitored by the patient's physician to enable the physician to track the patient's condition.

The impedance measuring circuit 120 is advantageously coupled to the switch bank 74 so that any desired electrode may be used. The current source 112 may be programmably configured between a desired pair of electrodes, and the voltage measuring circuit 90 may be programmably configured between the same or preferably a different pair of electrodes.

Exemplary Inventive Embodiments Overview

In the embodiments below, various configurations of electrodes are provided that permit measurements of left ventricular function to be made for both monitoring and therapy delivery. The different configurations can have a variety of polarities. For example, bipolar, tripolar and quadrapolar configurations can be used. Bipolar configurations are configurations that utilize any two suitable electrodes; tripolar configurations are configurations that use any three suitable electrodes; and quadrapolar configurations are configurations that use any four suitable configurations. The different configurations can be used to measure one or more physiological parameters for assessing or determining a patient's cardiac condition based on left heart impedance measurements. In the discussion that follows, certain specific electrode configurations are described to provide non-limiting examples of various bipolar, tripolar, and quadrapolar configurations that can be used to facilitate measurement of left ventricular function and the measurement of other parameters associated with heart function.

Respiration

Figure 3:
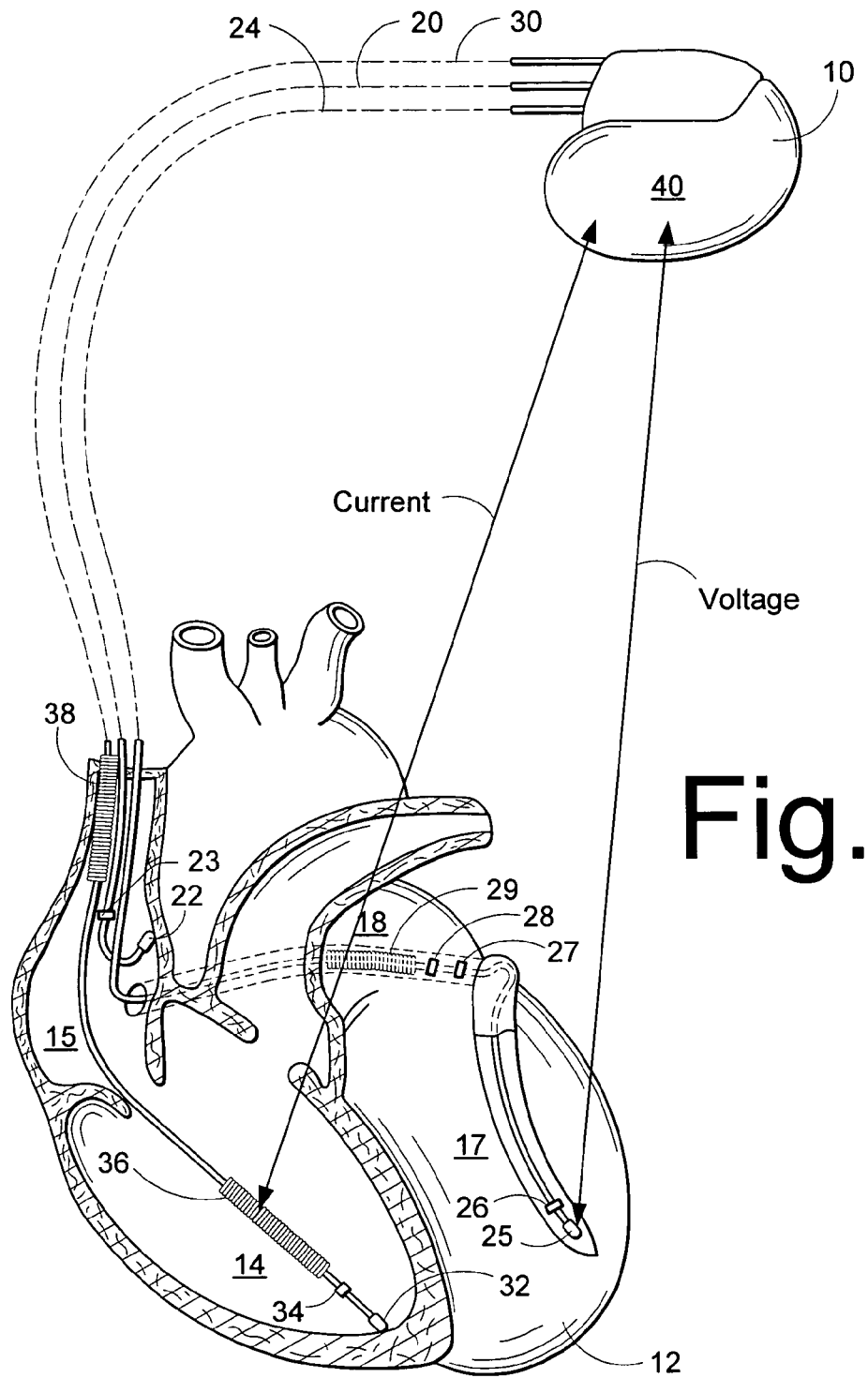
FIG. 3 is a reproduction of the patient's heart shown in FIG. 1 illustrating an electrode configuration that is suitable for use in ascertaining an impedance measure in accordance with one embodiment.

In conjunction with ventricular pacing of the heart, one parameter associated with the heart which is prominent in ascertaining the effectiveness of the cardiac pacing is respiration (or a respiration parameter, for example, tidal volume, respiration rate, minute ventilation or volume, abnormal or periodic breathing). This requires ascertaining the condition of the lung tissue and may also be measured by the device 10 illustrated in FIG. 3. This may be preferably accomplished by sourcing the current between the housing 40 and right ventricular coil electrode 36 while measuring the voltage between the left ventricular tip electrode 25 and housing 40.

Figure 4:
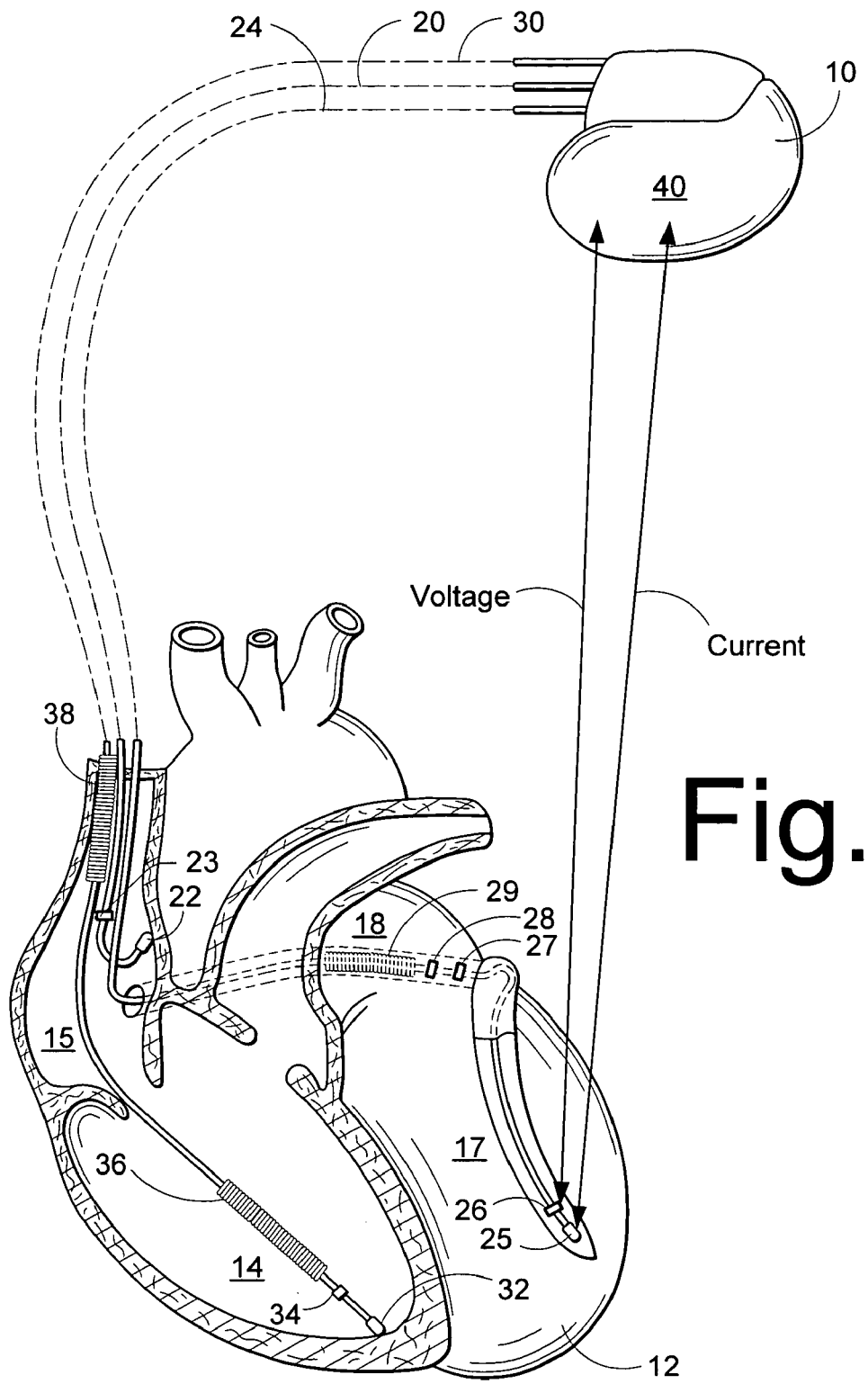
FIG. 4 is a reproduction of the patient's heart shown in FIG. 1 illustrating an electrode configuration that is suitable for use in ascertaining an impedance measure in accordance with one embodiment.

One limitation in the use of a pacing electrode, or a pacing electrode pair, in the cardiac vein is that the local impedance is influenced by many factors. With the system illustrated in FIG. 4, a three-point impedance measurement is obtained which is less affected by the local impedance of the electrode or electrodes in the great vein. As a result, an accurate measure of the left ventricular impedance is obtained to provide corresponding accurate monitoring of stroke volume and the respiration parameter.

In measuring the respiration parameter, a current path is established between the left ventricular tip electrode 25 and the housing 40. Once established, the voltage measuring circuit measures the voltage between the left ventricular ring electrode 26 and the housing 40. This effectively provides an impedance measurement corresponding to the respiration parameter. The resulting measured voltage signal will have both cardiac and respiratory components. However, the cardiac component will be smaller than that from intracardiac electrodes and can be readily filtered in a manner known in the art.

Figure 5:
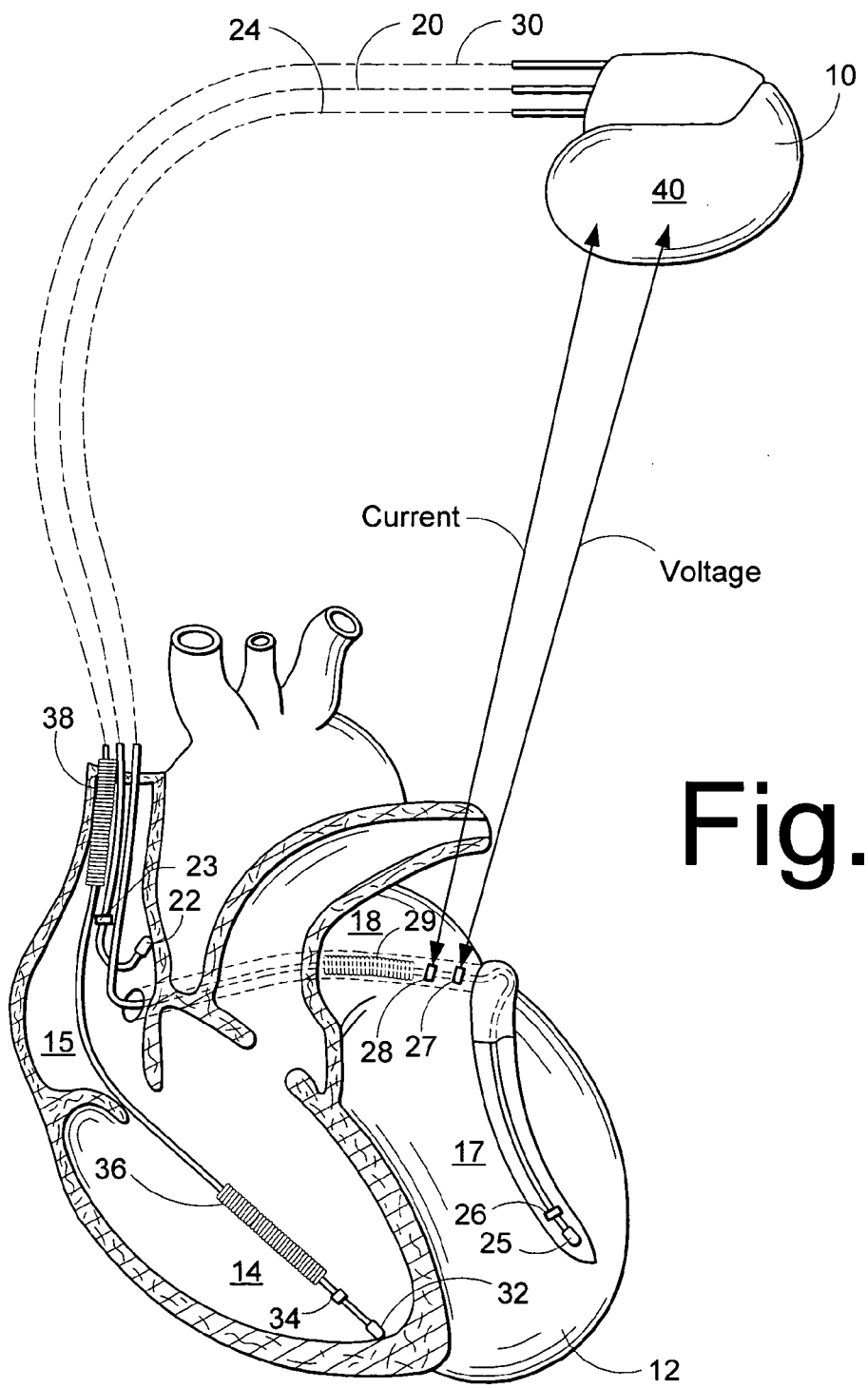
FIG. 5 is a reproduction of the patient's heart shown in FIG. 1 illustrating an electrode configuration that is suitable for use in ascertaining an impedance measure in accordance with one embodiment.

FIG. 5 shows another electrode configuration that can be used to measure impedance. In this configuration, a current path is established between left atrial ring electrode 28 and the housing 40. The voltage measuring circuit then measures the voltage between the left atrial ring electrode 27 and the housing 40.

Figure 6:
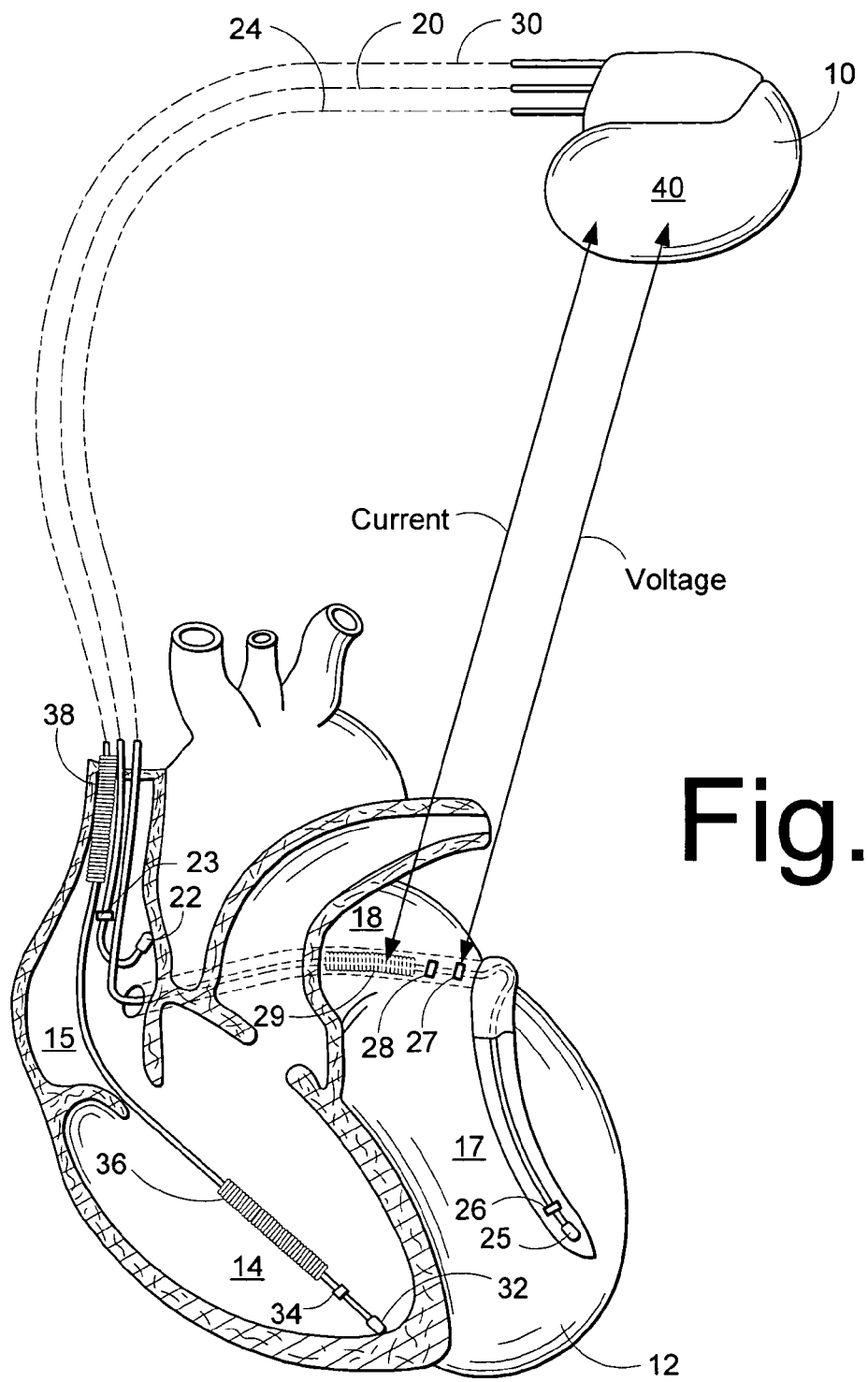
FIG. 6 is a reproduction of the patient's heart shown in FIG. 1 illustrating an electrode configuration that is suitable for use in ascertaining an impedance measure in accordance with one embodiment.

FIG. 6 shows another electrode configuration that can be used to measure impedance. In this configuration, a current path is established between left atrial coil electrode 29 and the housing 40. The voltage measuring circuit then measures the voltage between the left atrial ring electrode 27 and the housing 40.

Figure 7:
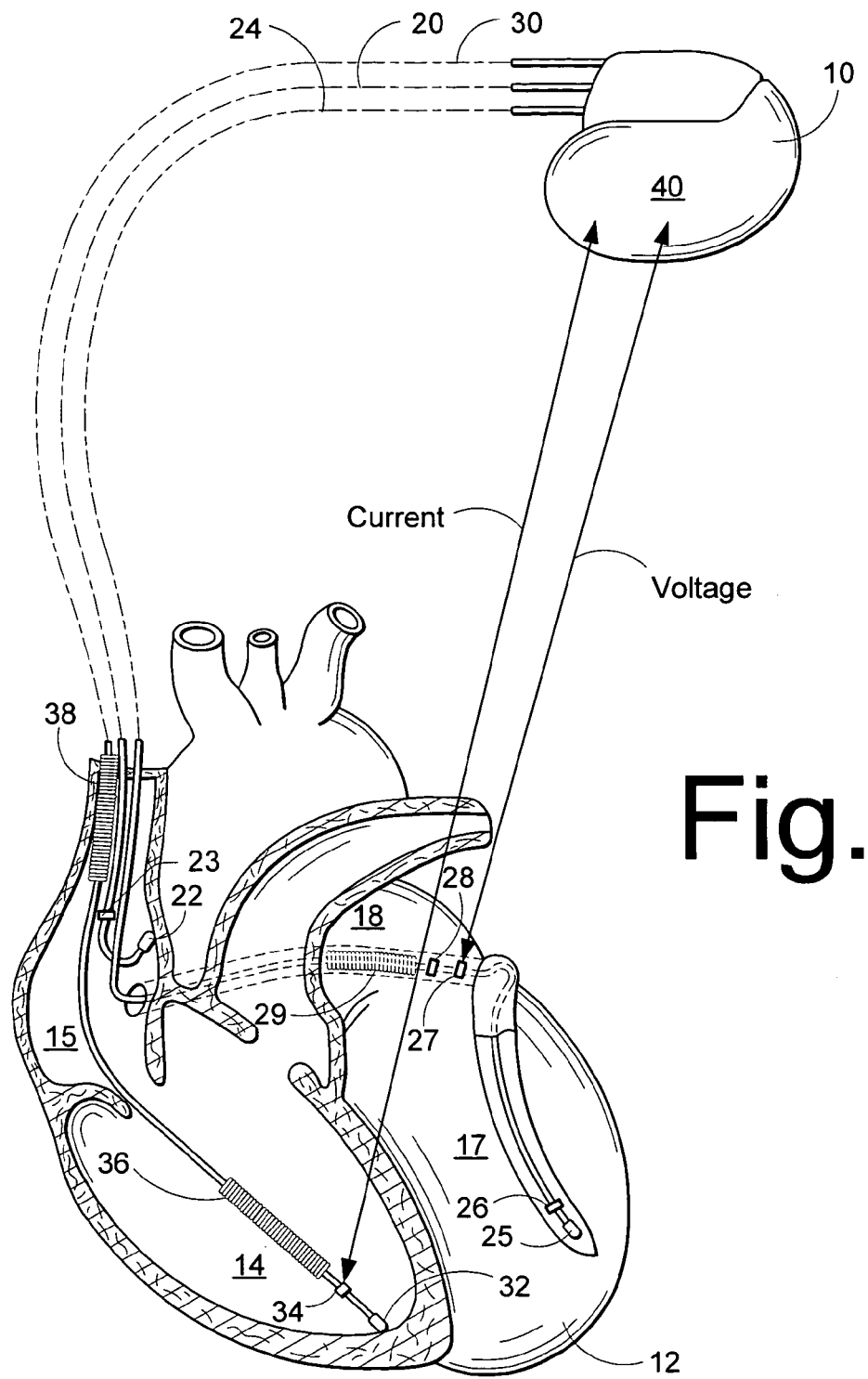
FIG. 7 is a reproduction of the patient's heart shown in FIG. 1 illustrating an electrode configuration that is suitable for use in ascertaining an impedance measure in accordance with one embodiment.

FIG. 7 shows a tripolar electrode configuration that can be used to measure impedance. In this configuration, a current path is established between right ventricular ring electrode 34 and the housing 40. The voltage measuring circuit then measures the voltage between the left atrial ring electrode 27 and the housing 40.

Figure 8:
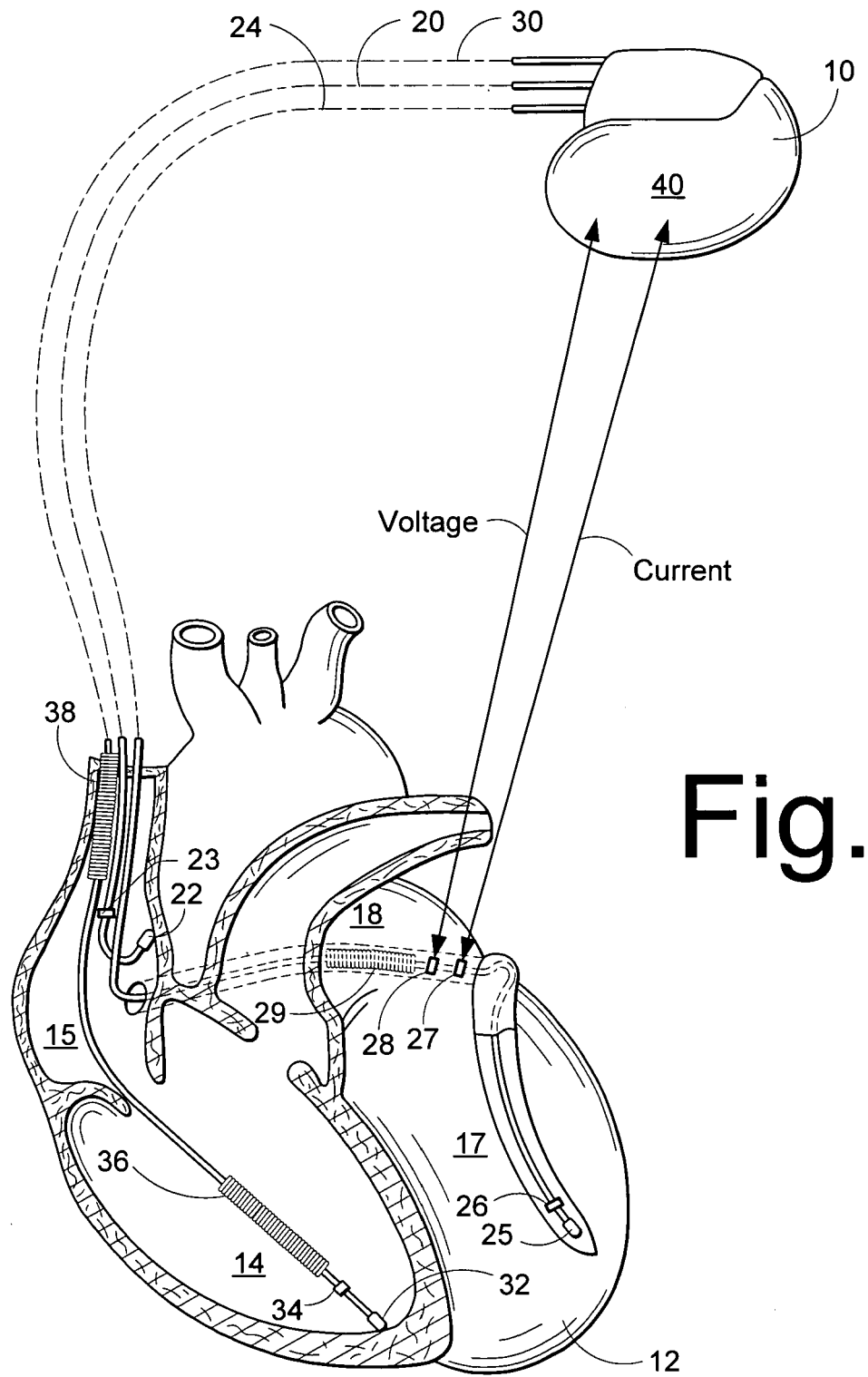
FIG. 8 is a reproduction of the patient's heart shown in FIG. 1 illustrating an electrode configuration that is suitable for use in ascertaining an impedance measure in accordance with one embodiment.

Alternatively, as will be appreciated by those skilled in the art, left atrial ring electrodes 27 and 28 can be utilized for the respiration parameter measurements. In this case, shown in FIG. 8, the electrical current path is established between the first atrial ring electrode 27 and the housing 40 and the resulting voltage is measured between the second atrial ring electrode 28 and the housing 40. As will also be appreciated by those skilled in the art, an alternative embodiment could employ a single electrode in a cardiac vein with appropriate filtering to extract the respiration parameter component of the impedance signal.

Left Ventricular Wall Dynamics

Figure 9:
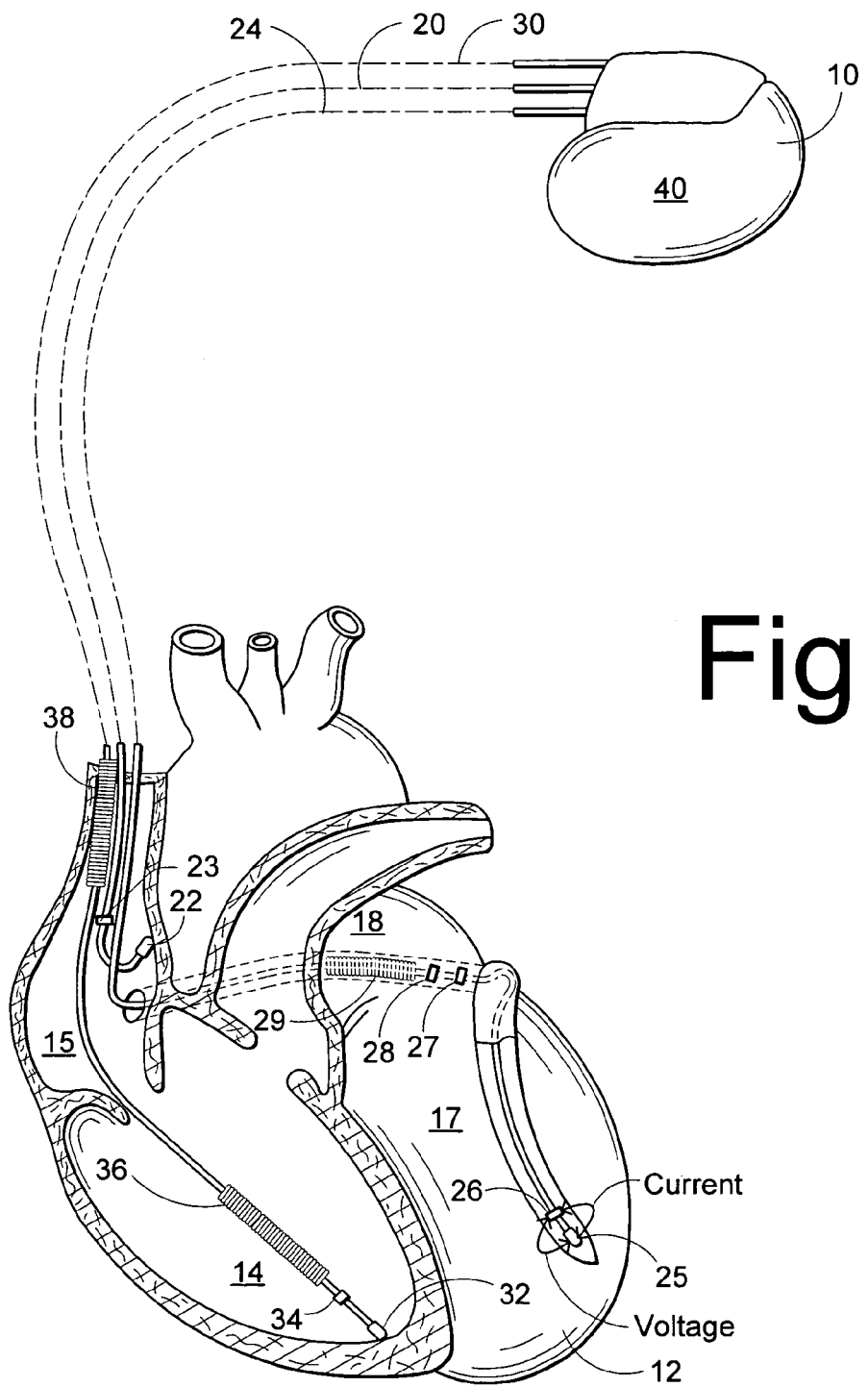
FIG. 9 is a reproduction of the patient's heart shown in FIG. 1 illustrating an electrode configuration that is suitable for use in ascertaining an impedance measure in accordance with one embodiment.

In an alternate embodiment, shown in FIG. 9, the device 10 can be coupled to a different electrode configuration for measuring left ventricular wall dynamics. Here it will be seen that the current source 112 is coupled between the left ventricular ring electrode 26 and the left ventricular tip electrode 25. The voltage measuring circuit 90 is also coupled between left ventricular ring electrode 26 and left ventricular tip electrode 25. Since the left ventricular electrodes 25 and 26 are preferably positioned so as to be located on the left ventricular free wall, the voltage signal measured by the voltage measuring circuit 90 will predominantly represent myocardium impedance for measuring left ventricular wall dynamics, such as the wall thickness.

Figure 10:
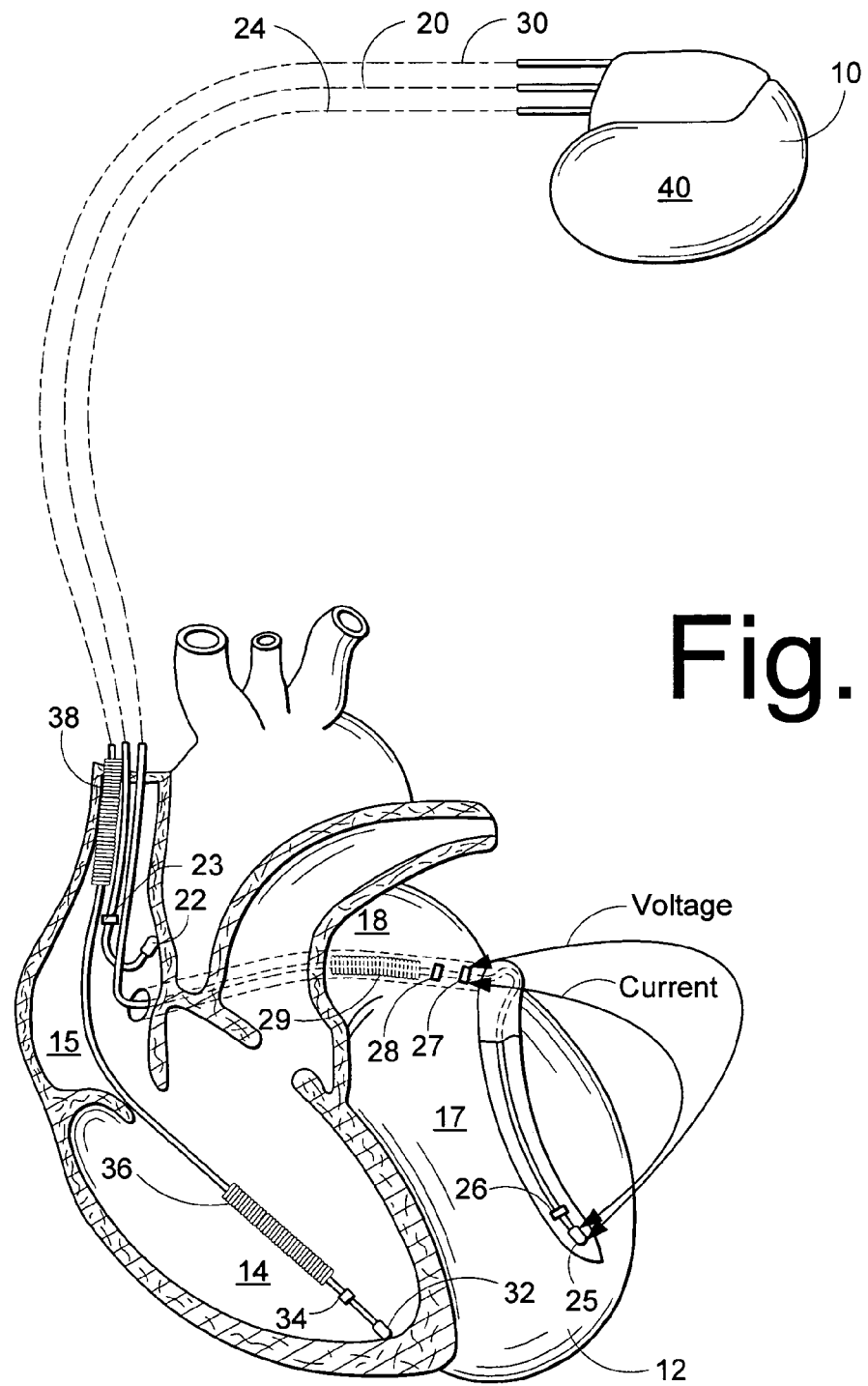
FIG. 10 is a reproduction of the patient's heart shown in FIG. 1 illustrating an electrode configuration that is suitable for use in ascertaining an impedance measure in accordance with one embodiment.

FIG. 10 shows an alternate bipolar electrode configuration that can be utilized to measure impedance for measuring left ventricular wall dynamics. In this embodiment, the current source 112 is coupled between the left atrial ring electrode 27 and the left ventricular tip electrode 25. The voltage measuring circuit 90 is coupled between the left atrial ring electrode 27 and the left ventricular tip electrode 25.

FIG. 11 shows an alternate tripolar electrode configuration that can be utilized to measure impedance for measuring left ventricular wall dynamics. In this embodiment, the current source 112 is coupled between the left atrial ring electrode 27 and the left ventricular tip electrode 25. The voltage measuring circuit 90 is coupled between the left atrial ring electrode 28 and the left ventricular tip electrode 25.

Figure 12:
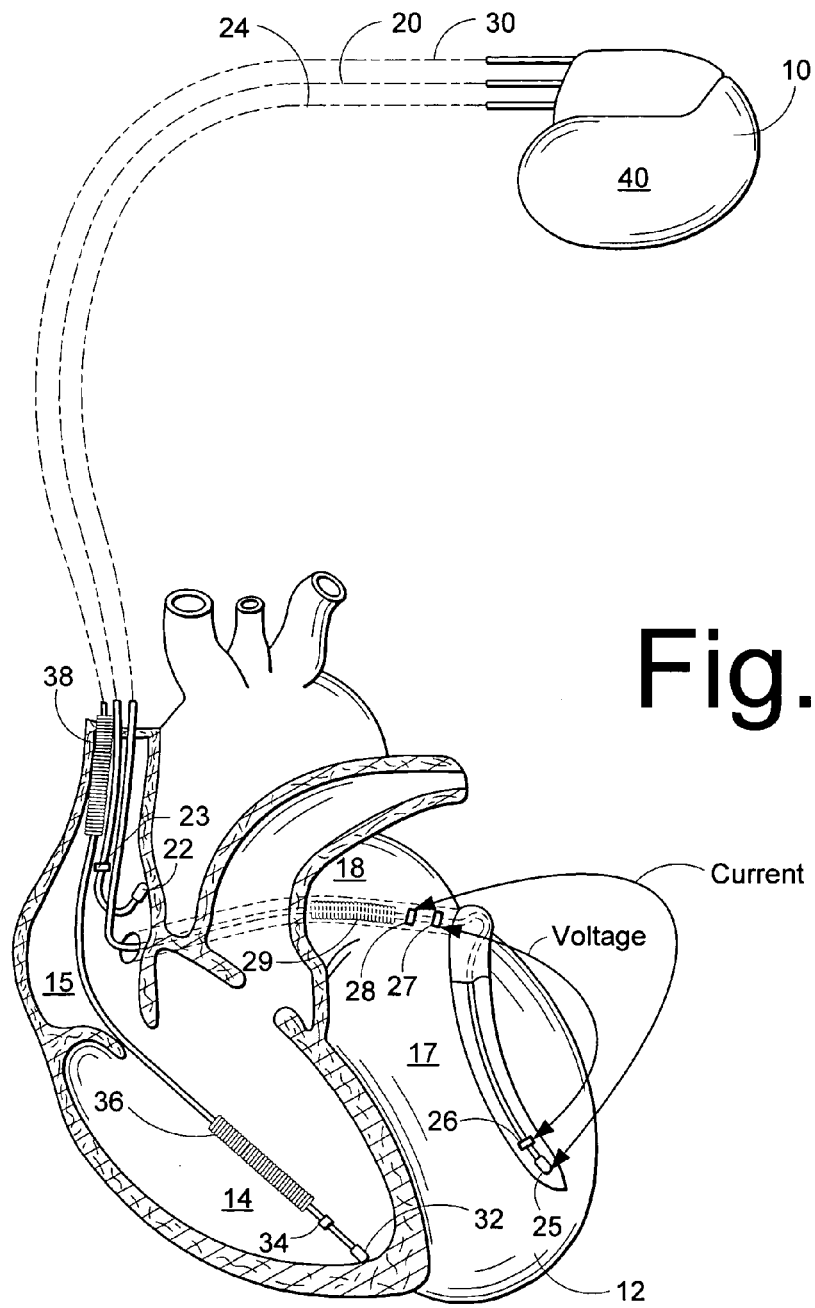
FIG. 12 is a reproduction of the patient's heart shown in FIG. 1 illustrating an electrode configuration that is suitable for use in ascertaining an impedance measure in accordance with one embodiment.

FIG. 12 shows an alternate quadrapolar electrode configuration that can be utilized to measure impedance for measuring left ventricular wall dynamics. In this embodiment, the current source 112 is coupled between the left atrial ring electrode 28 and the left ventricular tip electrode 25. The voltage measuring circuit 90 is coupled between the left atrial ring electrode 27 and the left ventricular ring electrode 26.

Figure 13:
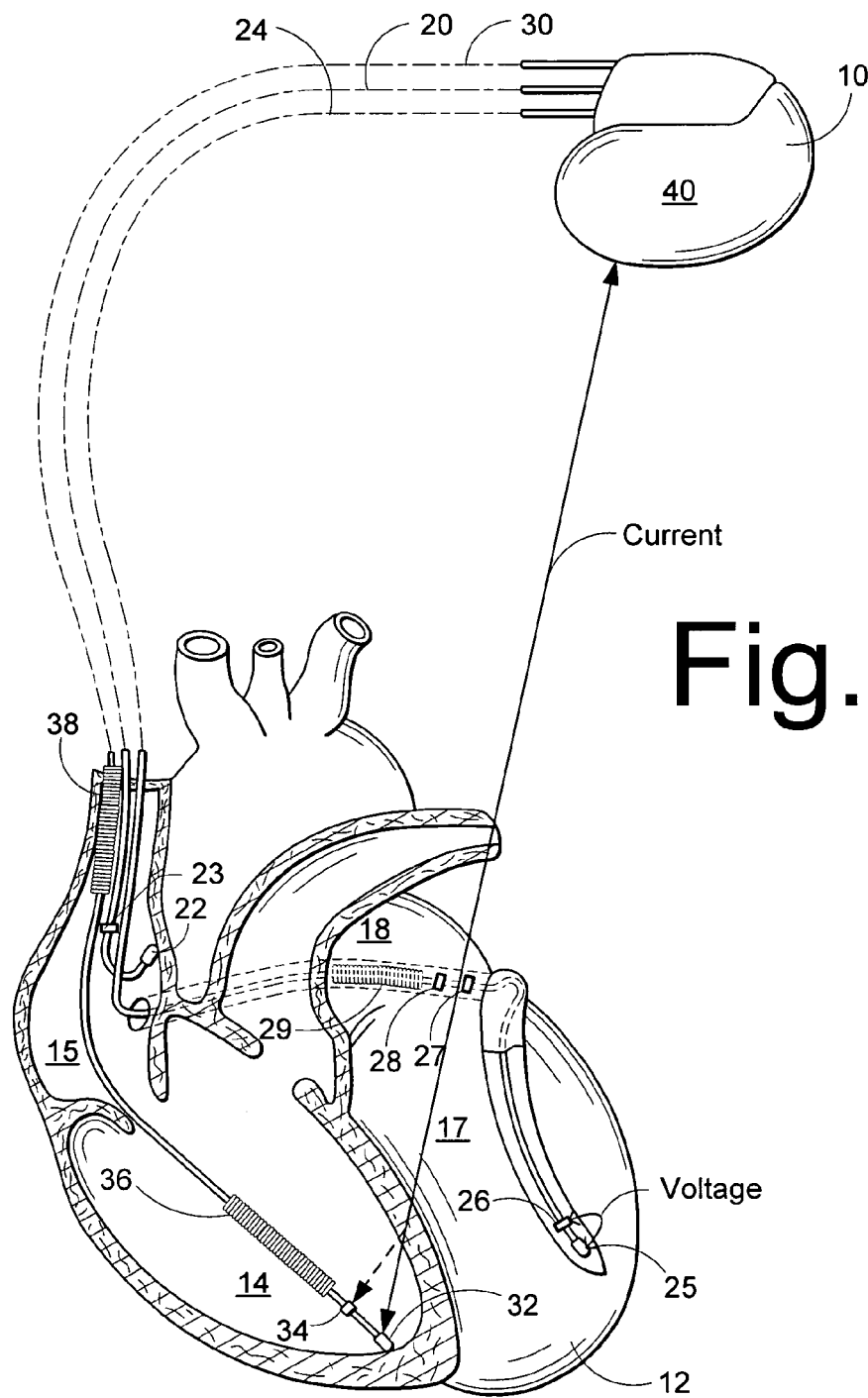
FIG. 13 is a reproduction of the patient's heart shown in FIG. 1 illustrating an electrode configuration that is suitable for use in ascertaining an impedance measure in accordance with one embodiment.

Alternatively, the current source 112 can be coupled between a right ventricular electrode 32 or 34 and the housing 40 with voltage measurement still performed between electrodes 26 and 25 as shown in FIG. 13. As will be appreciated by those skilled in the art, an alternative embodiment could employ a single electrode within a cardiac vein on the left ventricular free wall and appropriate filtering to extract the cardiac component in the impedance signal.

Figure 14:
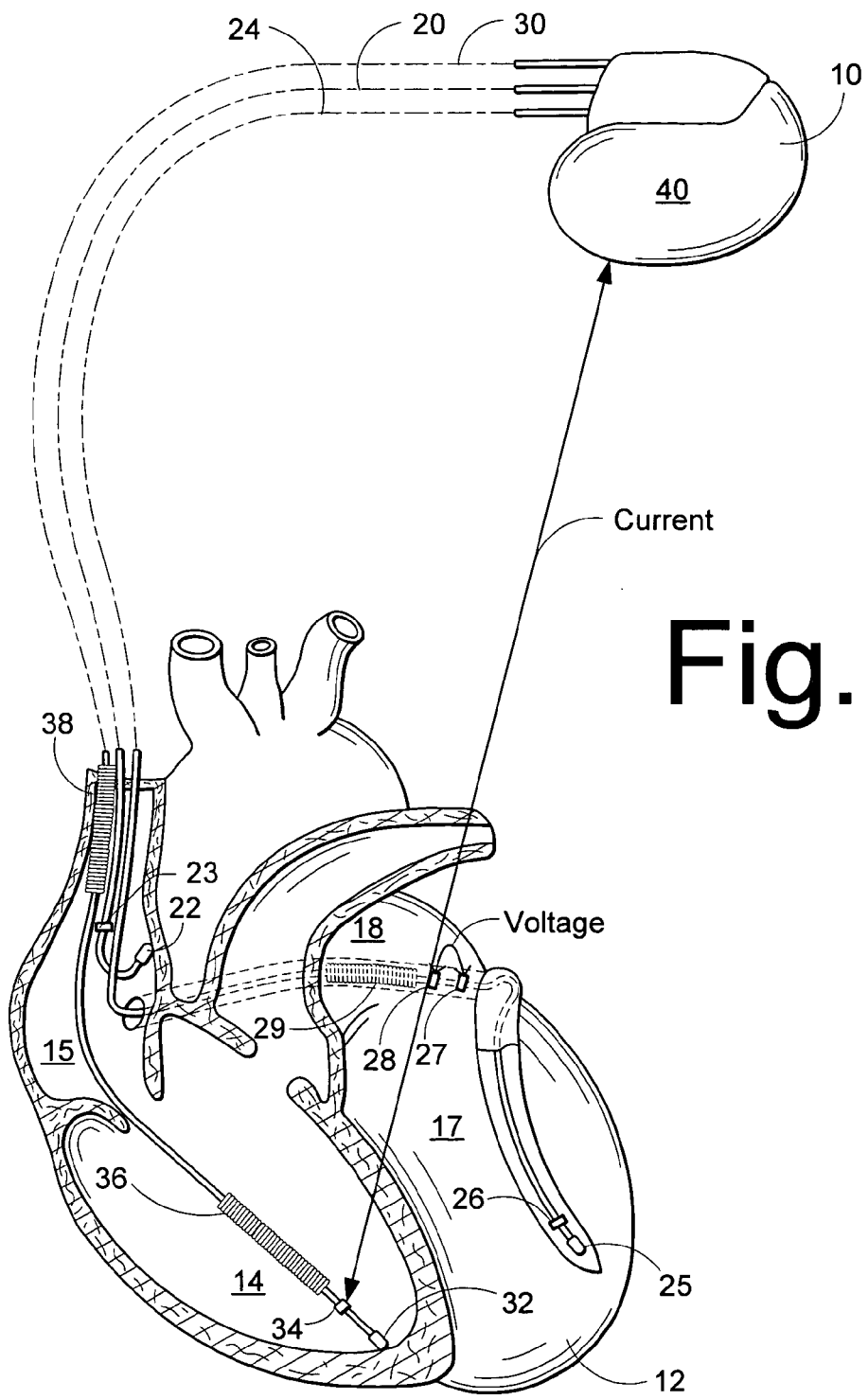
FIG. 14 is a reproduction of the patient's heart shown in FIG. 1 illustrating an electrode configuration that is suitable for use in ascertaining an impedance measure in accordance with one embodiment.

FIG. 14 shows an alternate tripolar electrode configuration that can be utilized to measure impedance for measuring left ventricular wall dynamics. In this embodiment, the current source 112 is coupled between the right ventricular ring electrode 34 and the housing 40. The voltage measuring circuit 90 is coupled between the left atrial ring electrodes 27, 28.

Figure 15:
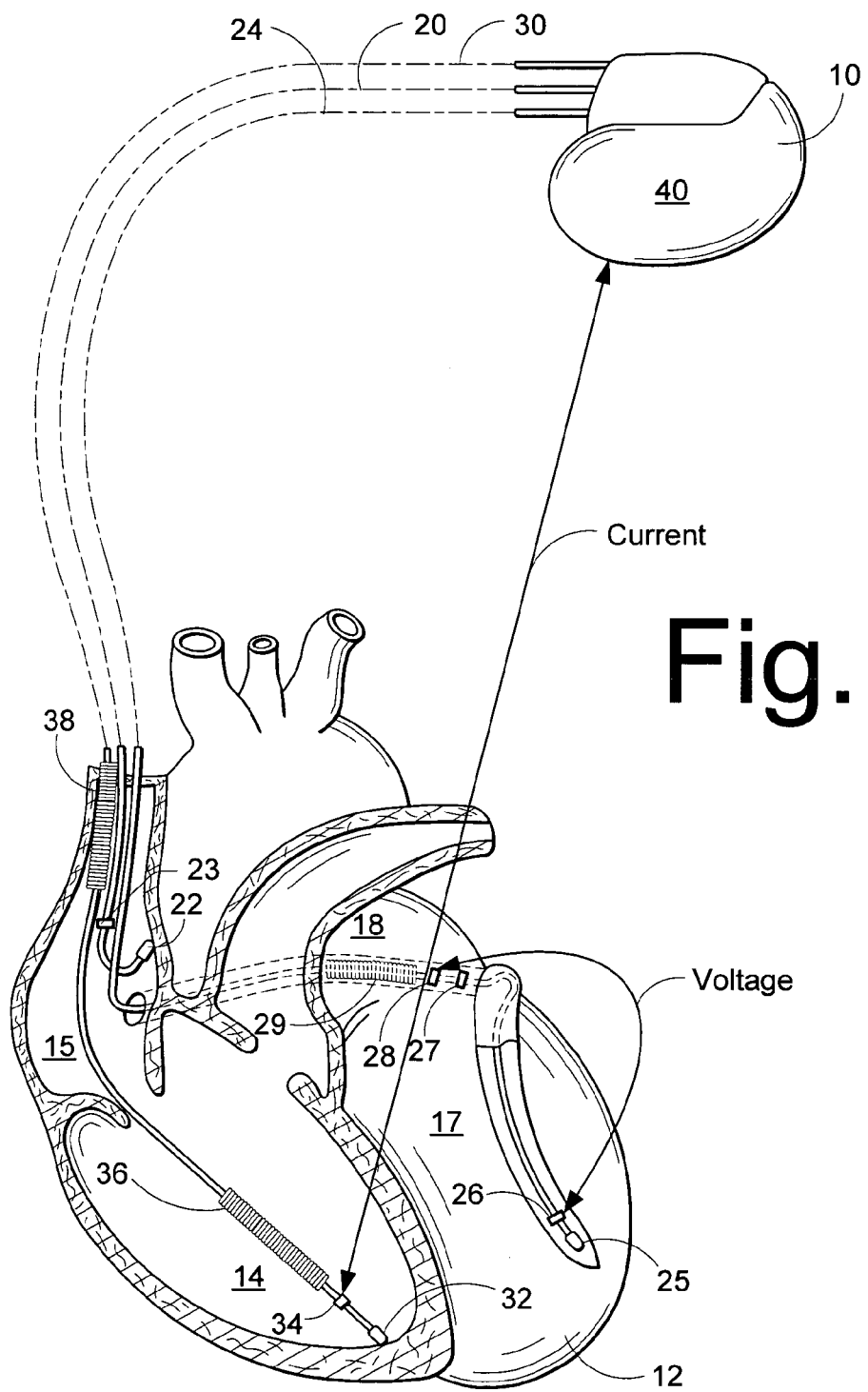
FIG. 15 is a reproduction of the patient's heart shown in FIG. 1 illustrating an electrode configuration that is suitable for use in ascertaining an impedance measure in accordance with one embodiment.

FIG. 15 shows an alternate electrode configuration that can be utilized to measure impedance for measuring left ventricular wall dynamics. In this embodiment, the current source 112 is coupled between the right ventricular ring electrode 34 and the housing 40. The voltage measuring circuit 90 is coupled between the left atrial ring electrode 28 and the left ventricular ring electrode 26.

Left Ventricular Volume Measurements

The current source 112 and voltage measuring circuit 90 may be employed in still further different configurations that facilitate left ventricular volume measurements. Here it will be seen that the left ventricular volume measurements are made with electrode pairs which are selected to measure a cross-section of the left ventricle. This can be done by determining the trans-chamber impedance.

Figure 16:
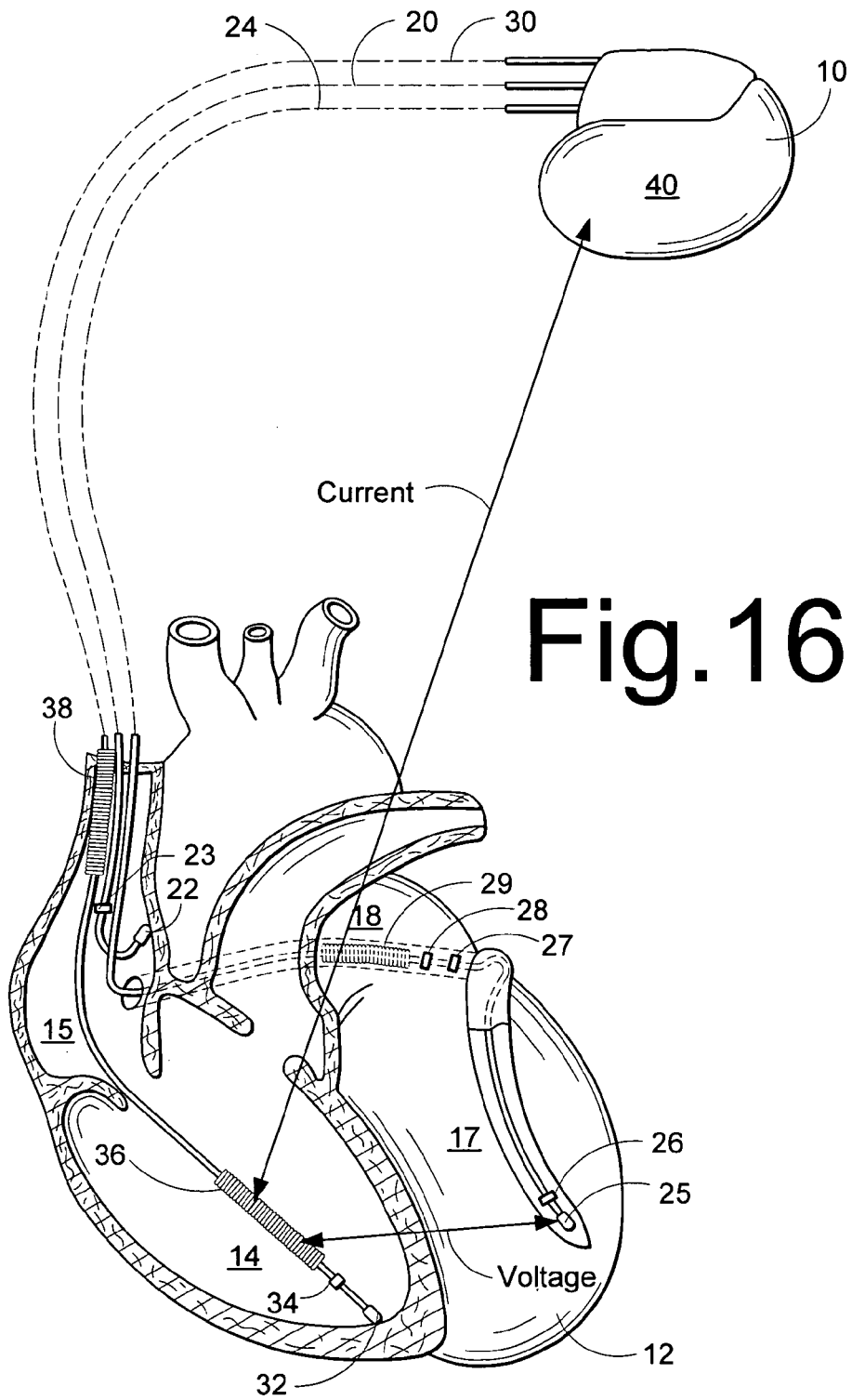
FIG. 16 is a reproduction of the patient's heart shown in FIG. 1 illustrating an electrode configuration that is suitable for use in ascertaining an impedance measure in accordance with one embodiment.

For example, FIG. 16 shows a configuration that can be utilized to monitor stroke volume. In this configuration, the current source 112 can be configured to provide an alternating current between the housing 40 and the right ventricular coil electrode 36. As this current is established, the voltage across the left ventricle is measured between the left ventricular tip electrode 25 and the right ventricular coil electrode 36. This gives an accurate measure of the left ventricular impedance and will provide an accurate contraction signature.

Figure 17:
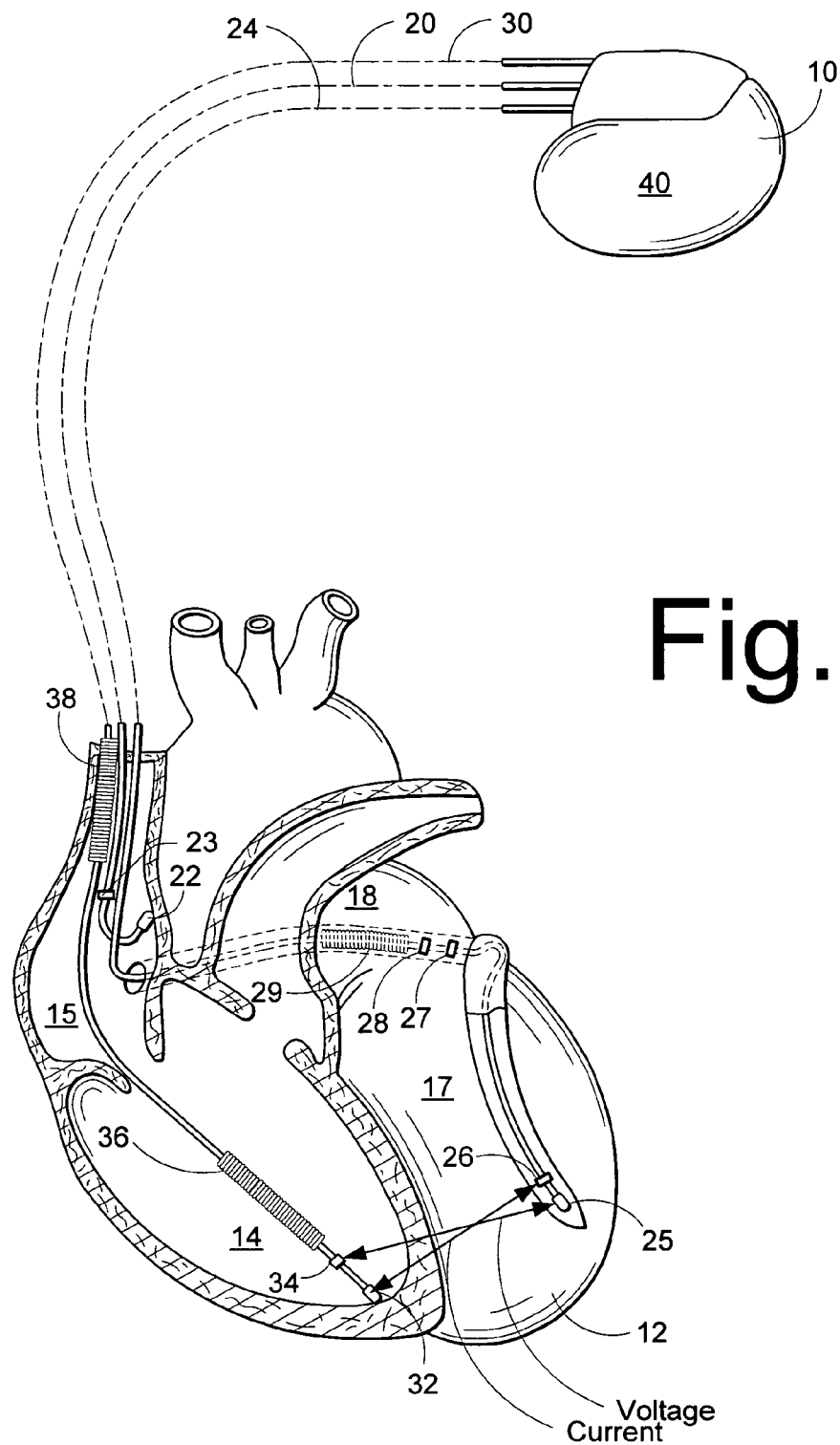
FIG. 17 is a reproduction of the patient's heart shown in FIG. 1 illustrating an electrode configuration that is suitable for use in ascertaining an impedance measure in accordance with one embodiment.

FIG. 17 shows another configuration that can be utilized to determine trans-chamber impedance. Here, the current source 112 is coupled between the right ventricular tip electrode 32 and the left ventricular ring electrode 26, while the voltage measuring circuit 90 is coupled between the right ventricular ring electrode 34 and the left ventricular tip electrode 25.

Figure 18:
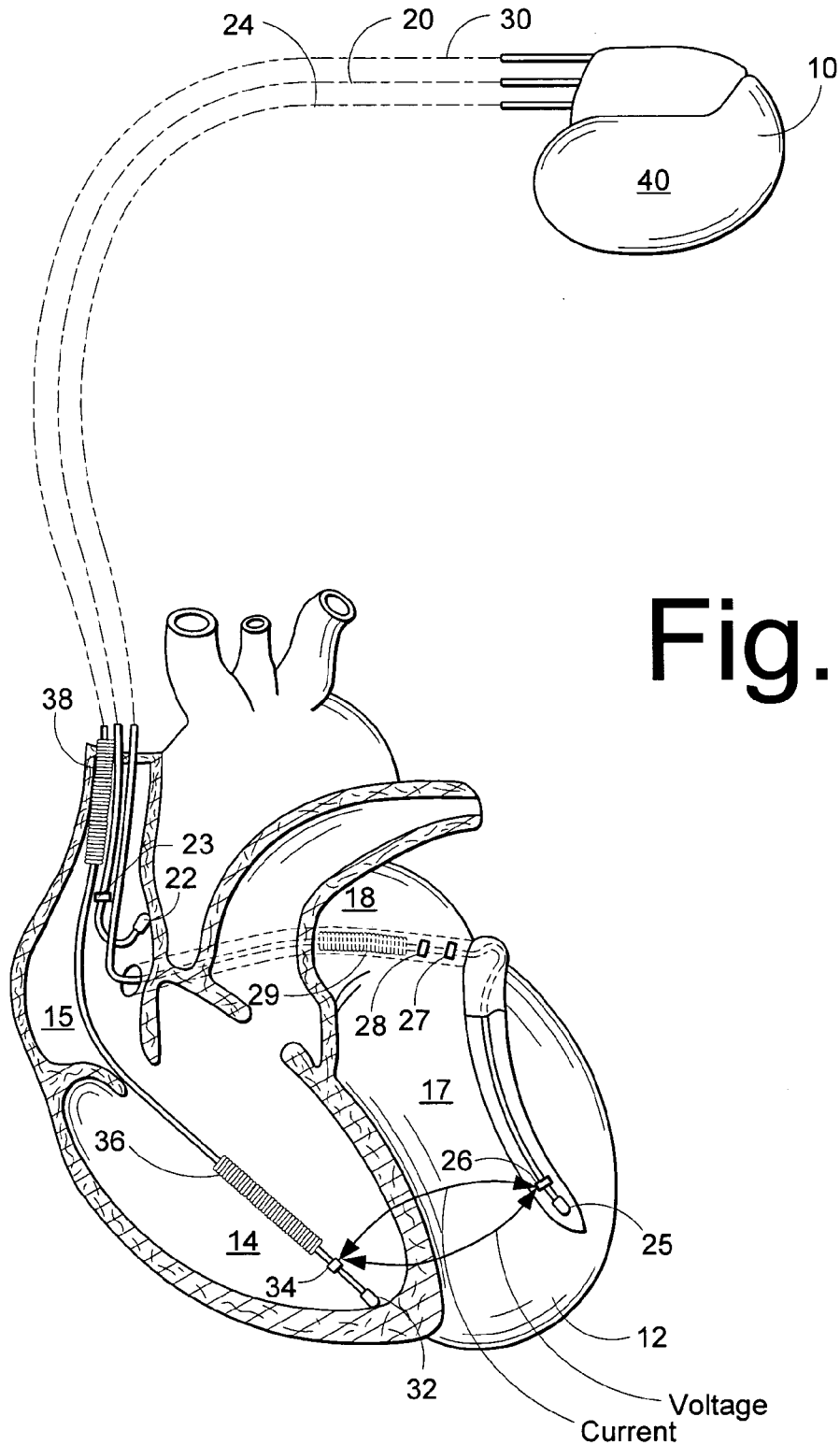
FIG. 18 is a reproduction of the patient's heart shown in FIG. 1 illustrating an electrode configuration that is suitable for use in ascertaining an impedance measure in accordance with one embodiment.
Figure 19:
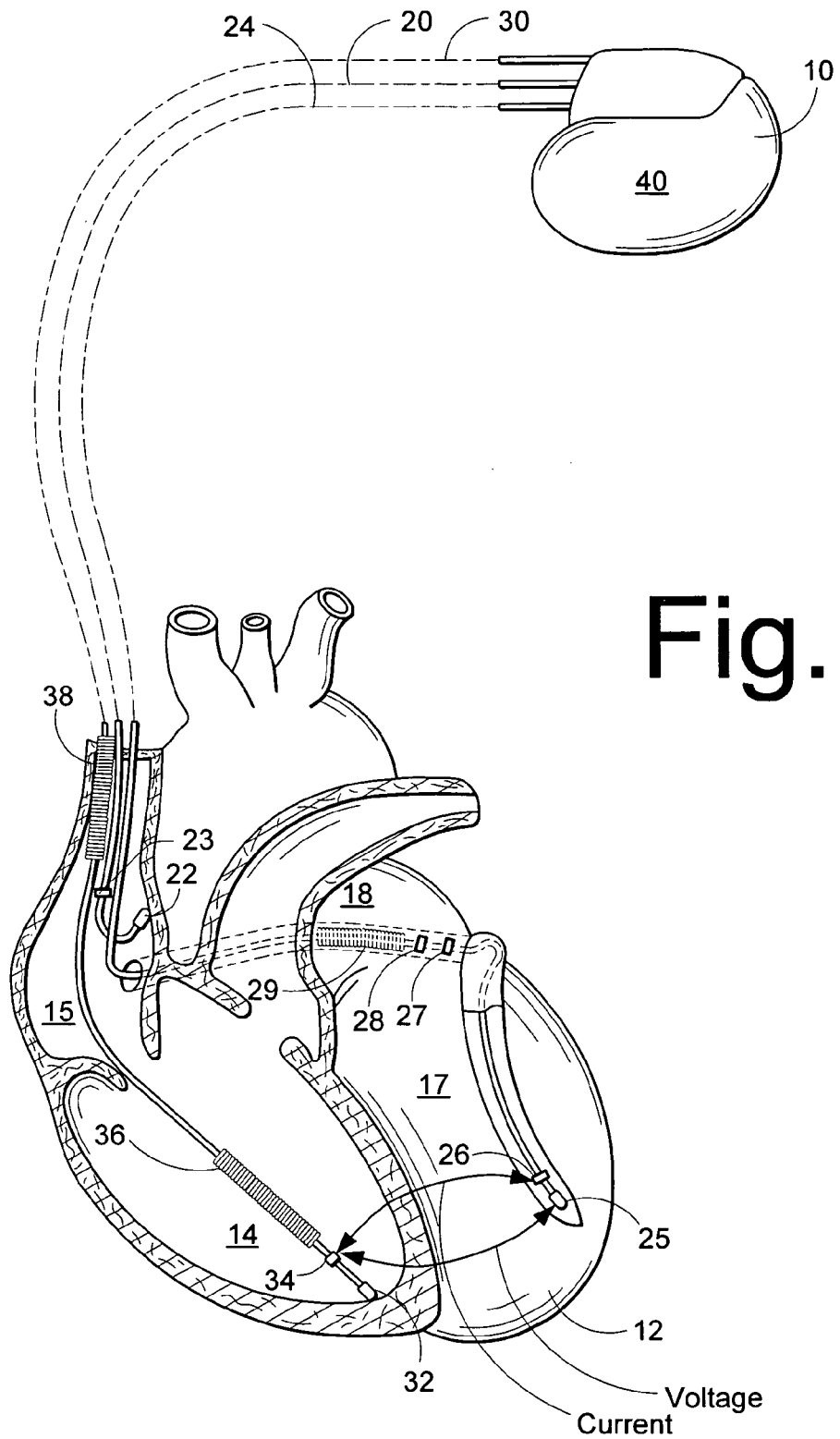
FIG. 19 is a reproduction of the patient's heart shown in FIG. 1 illustrating an electrode configuration that is suitable for use in ascertaining an impedance measure in accordance with one embodiment.

FIG. 18 shows a bipolar configuration that can be utilized to determine trans-chamber impedance. Here, the current source 112 is coupled between the right ventricular ring electrode 34 and the left ventricular ring electrode 26, and the voltage measuring circuit 90 is coupled between the right ventricular ring electrode 34 and the left ventricular ring electrode 26.

In accordance with the embodiment shown in FIG. 18, the current source 112 is coupled between the right ventricular ring electrode 34 and the left ventricular ring electrode 26, while the voltage measuring circuit 90 is coupled between the right ventricular ring electrode 34 and the left ventricular tip electrode 25.

Preferably, the voltage measuring circuitry 90 measures the voltage between the right ventricular electrode 32 or 34 which was not used in the establishing of the electrical current path and the left ventricular tip electrode 25. The voltage signal thus measured will be representative of the cross-section of the left ventricle and yield an accurate representation of the left ventricular volume.

Figure 20:
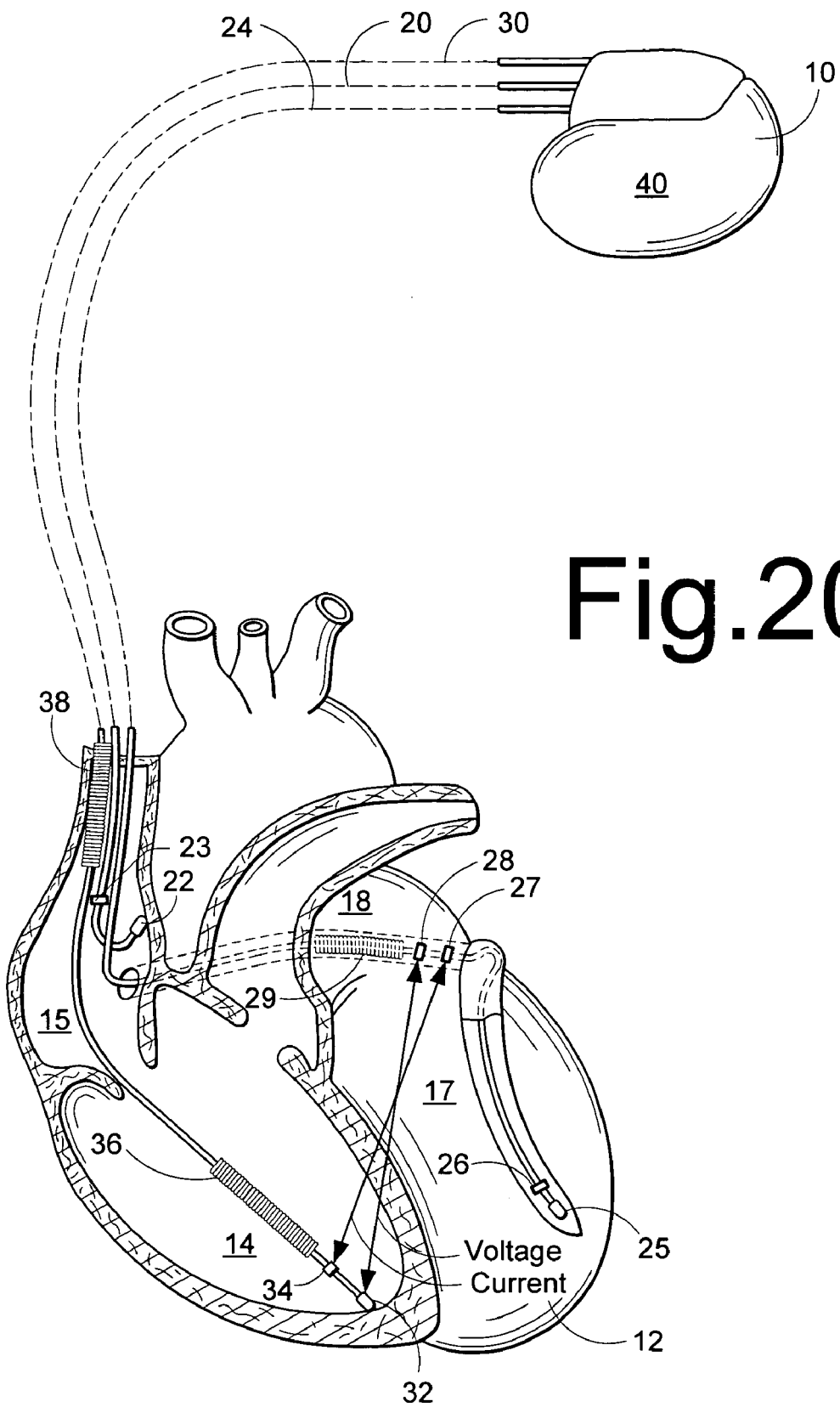
FIG. 20 is a reproduction of the patient's heart shown in FIG. 1 illustrating an electrode configuration that is suitable for use in ascertaining an impedance measure in accordance with one embodiment.

In yet another alternative embodiment for measuring left ventricular volume (a quadrapolar configuration), shown in FIG. 20, it will be noted that the current source 112 is coupled between the right ventricular ring electrode 34 and the first left atrial ring electrode 27, while the voltage measuring circuit 90 is coupled between the right ventricular tip electrode 32 and the second left atrial ring electrode 28.

Figure 21:
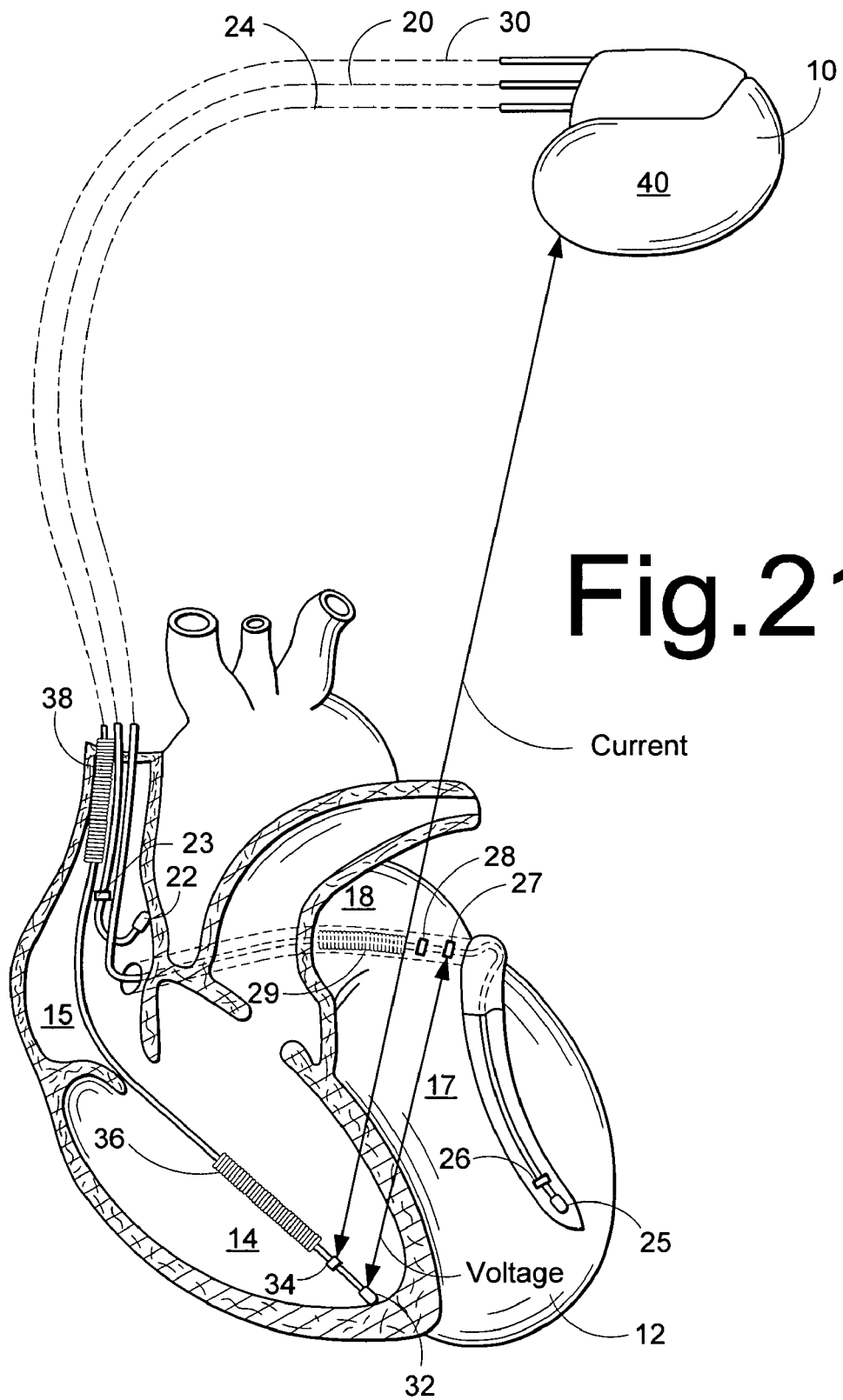
FIG. 21 is a reproduction of the patient's heart shown in FIG. 1 illustrating an electrode configuration that is suitable for use in ascertaining an impedance measure in accordance with one embodiment.

Alternatively, shown in FIG. 21, the current source 112 can be coupled between the right ventricular ring electrode 34 and the housing 40, while the voltage measuring circuit 90 is coupled between the right ventricular tip electrode 32 and the second left atrial ring electrode 28.

Figure 22:
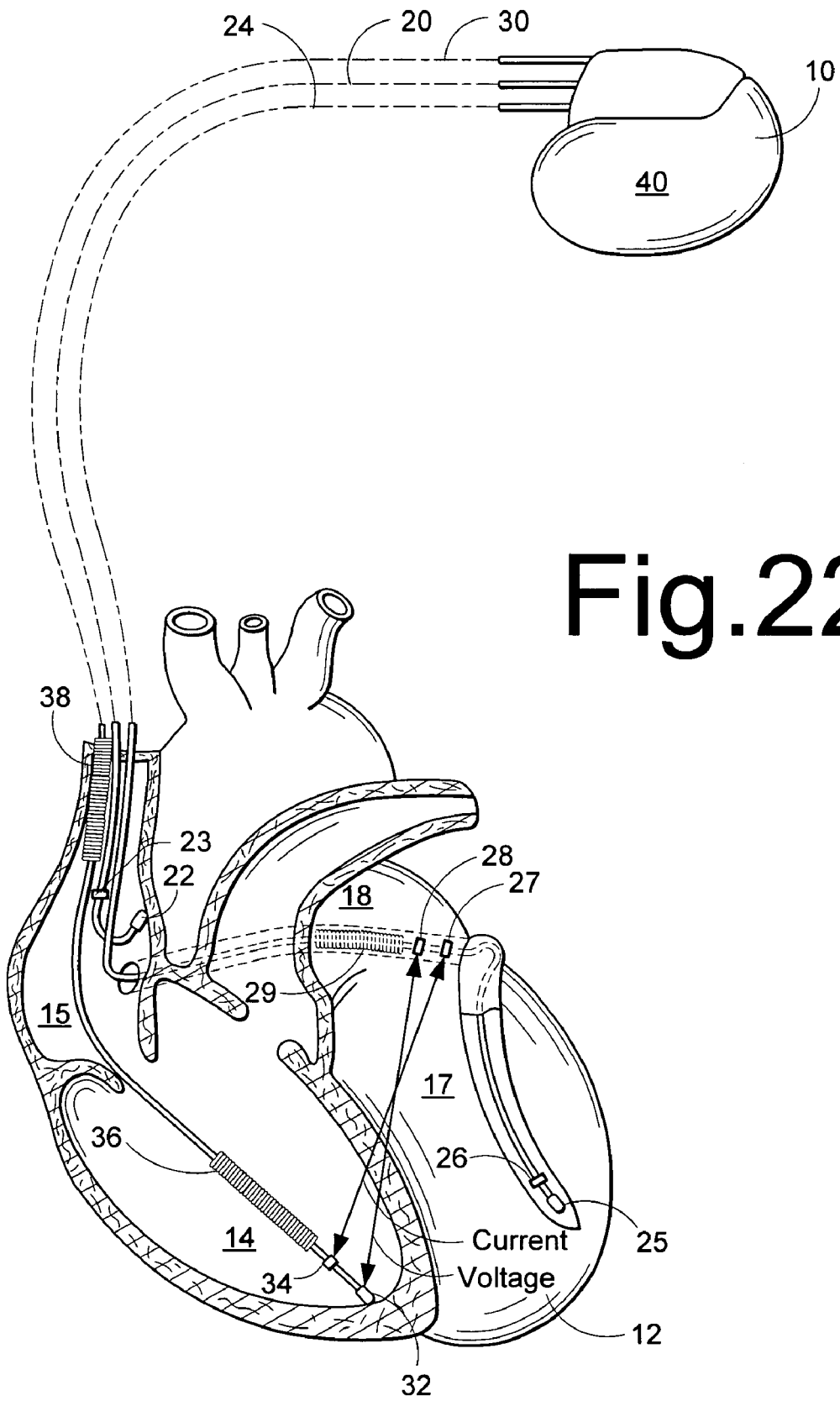
FIG. 22 is a reproduction of the patient's heart shown in FIG. 1 illustrating an electrode configuration that is suitable for use in ascertaining an impedance measure in accordance with one embodiment.

In yet another embodiment, a quadrapolar configuration shown in FIG. 22, is provided for measuring the left ventricular volume. Here, the current source 112 establishes an electrical current between the right ventricular ring electrode 34 and the first left atrial ring electrode 27. While this current is established, the voltage measuring circuit 90 measures the voltage between the right ventricular tip electrode 32 and the second left atrial ring electrode 28. The resulting voltage signal measured by the voltage measuring circuit 90 will represent the impedance across the cross-section of the left ventricle to provide an accurate representation of the left ventricular volume.

Various exemplary mechanisms optionally include use of an additional implanted device. Such exemplary mechanisms may obtain physiological information by measuring electrical signals across a fairly large volume of a body. Measurements may rely on impedance plethysmography or more particularly impedance cardiography techniques. Information obtained using such techniques may relate to cardiac performance (e.g., stroke volume, etc.).

Figure 23:
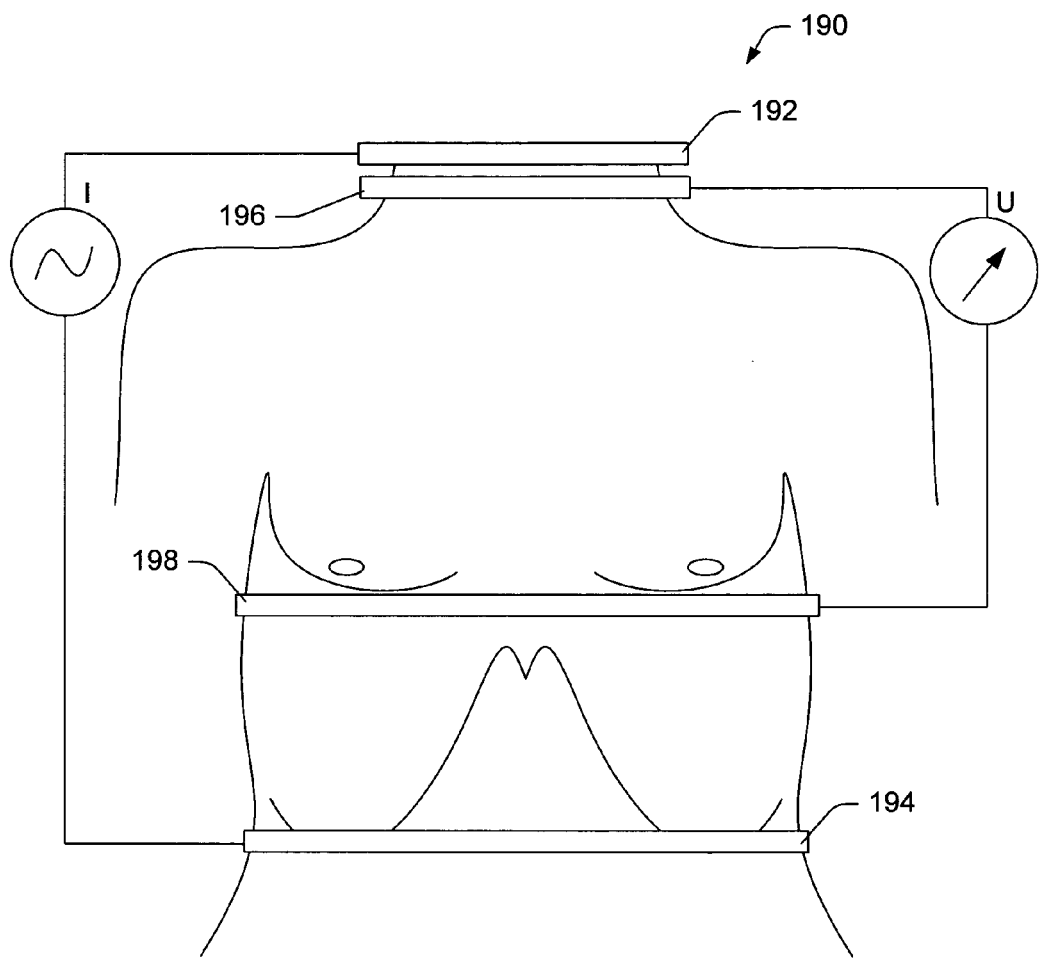
FIG. 23 is an approximate diagram of a conventional arrangement for impedance measurement.

Conventional techniques for impedance plethysmography typically rely on use of four electrodes: two for introduction of current and two for voltage or potential measurement. FIG. 23 shows a conventional arrangement 190 that includes two external pairs of electrodes. An outer pair of ring electrodes 192, 194 is used to introduce a current while an inner pair of ring electrodes 196, 198 is used to measure voltage or potential.

Knowledge of various values can allow for determination of macroscopic resistivity (e.g., impedance per unit volume). For example, macroscopic resistivity may be derived from the spatial distribution of conductivity weighted by the dot product of the lead fields of the current and voltage electrodes. Such a derivation may rely on measured voltage per applied current.

As already mentioned, current may be introduced using a pair of electrodes and a voltage or potential measurement made using a pair of electrodes. In general, the voltage measurement pair uses at least one electrode not used in the current introduction pair and, as shown in various examples, there may be no common electrode(s) between the current electrodes and the voltage electrodes. In the latter case, if the current introduction electrodes are different from those of the voltage measurement electrodes, the sensitivity distribution is the dot product of the lead fields of the voltage electrodes and the current electrodes.

With respect to various exemplary mechanisms, depending on arrangement of selected implanted electrodes, current introduction and potential measurement may be directed to a particular volume or region. Further, the aforementioned dot product may be negative for a particular volume such that an increase in conductivity is associated with an increase in impedance.

Various exemplary mechanisms optionally determine a baseline from which changes may be tracked. Accordingly, such exemplary mechanisms may account for a positive dot product or a negative dot product in determining how one or more physiologic parameters may be changing over time, wherein the time scale is selected in accordance with the expected rate of change in an improving or deteriorating physiologic parameter. For example, if an exemplary method aims to track enlargement of a ventricle as associated with progression of congestive heart failure, then the selected time scale, signal averaging, number of samples, etc., may be fairly large. On the other hand, if an exemplary method aims to track changes in cardiac output during a treadmill test, then the selected time scale, signal averaging, number of samples, etc., may be smaller. In general, electrode selection and signal processing account for signal characteristics and physiology under investigation.

An exemplary implantable device optionally includes one or more schemes for selecting electrodes and/or processing signals based on signal characteristics and/or physiology under investigation. Such schemes are typically implemented using hardware and/or software (e.g., consider a module operable with the programmable microcontroller 60 of FIG. 2).

Referring again to the conventional arrangement 190 of FIG. 23, a current frequency of up to approximately 100 kHz is typically used wherein measurement of voltage allows for determination of impedance. In general, conventional techniques (e.g., Kubicek four electrode technique, etc.) ignore the direct current component of the voltage and rely only on the time varying component of the voltage. Of particular interest is the time varying impedance.

The conventional arrangement 190 includes the outer pair of ring electrodes with one ring 192 placed around the neck and the other ring 194 placed around the abdomen 194 while the inner pair of ring electrodes has one ring 196 placed around the neck and the other ring 198 placed around the thorax at about the level of the joint between the xiphoid and the sternum.

Figure 24:
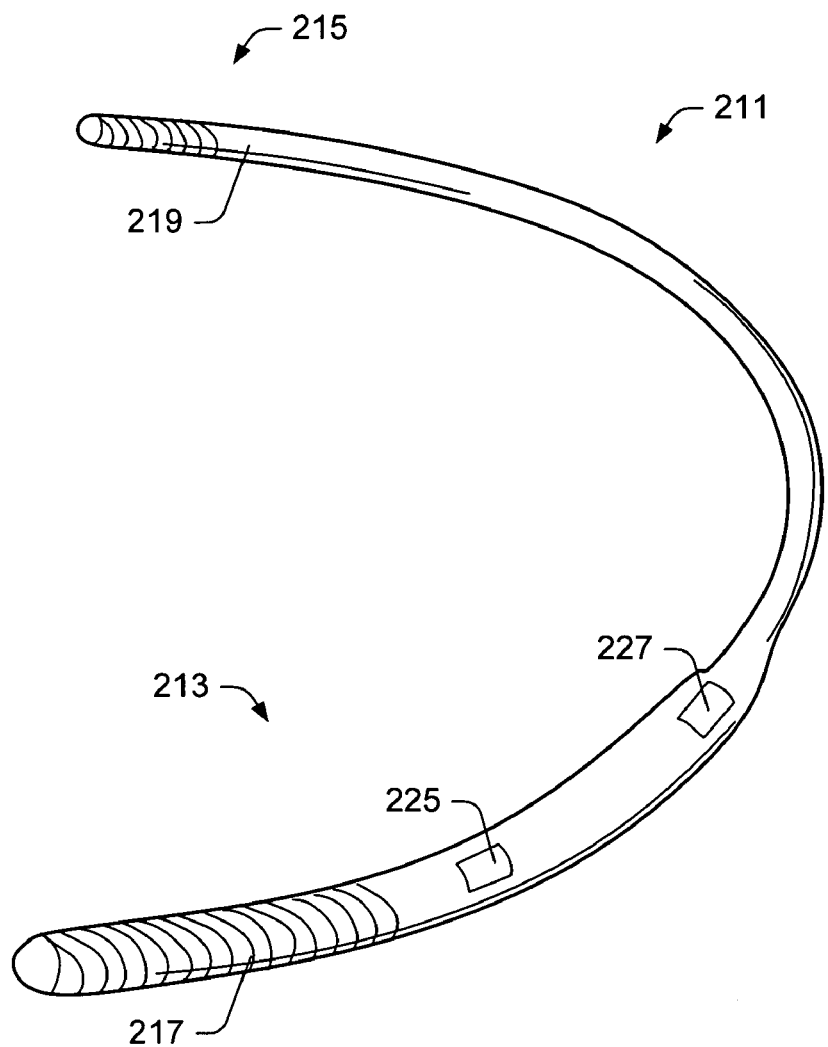
FIG. 24 is a diagram of a prior art unitary subcutaneous defibrillation device.

FIG. 24 shows a prior art device 211 as disclosed in U.S. Pat. No. 6,647,292, to Bardy et al. ('292 patent), which is incorporated by reference herein. The device 211 serves to illustrate a unitary subcutaneous cardiac defibrillation device. The device 211 has a first end 213 and a second end 215 wherein the first end 213 is thicker than the second end 215 and houses a power supply, capacitor and operational circuitry cardiac defibrillation. Defibrillation occurs through use of two cardioversion and/or defibrillation electrodes 217 and 219 located on the outer surface of the two ends of the housing. The length of the device 211, as stated in the '292 patent, will range from about 15 to about 50 cm and the coil cardioversion and/or defibrillation electrodes 217, 219 are about 5 to 10 cm in length. Located on the housing between the two cardioversion and/or defibrillation electrodes are two sense electrodes 225 and 227 wherein, according to the '292 patent, the spacing can range from 1 to 10 cm.

According to various exemplary methods, devices, systems, etc., disclosed herein, a cardiac defibrillation device that includes various features of the prior art device 211 optionally includes circuitry that allows for introduction of a current and/or measurement of voltage or potential. For example, an exemplary device includes a substantially elongated shape wherein two electrodes of the device have a spacing of about 10 cm or more. Such an exemplary device optionally includes a circuit that allows for communication with another implantable device. Such an exemplary device includes an ability to introduce a current between the two electrodes and/or to measure voltage or potential between the two electrodes.

Figure 25:
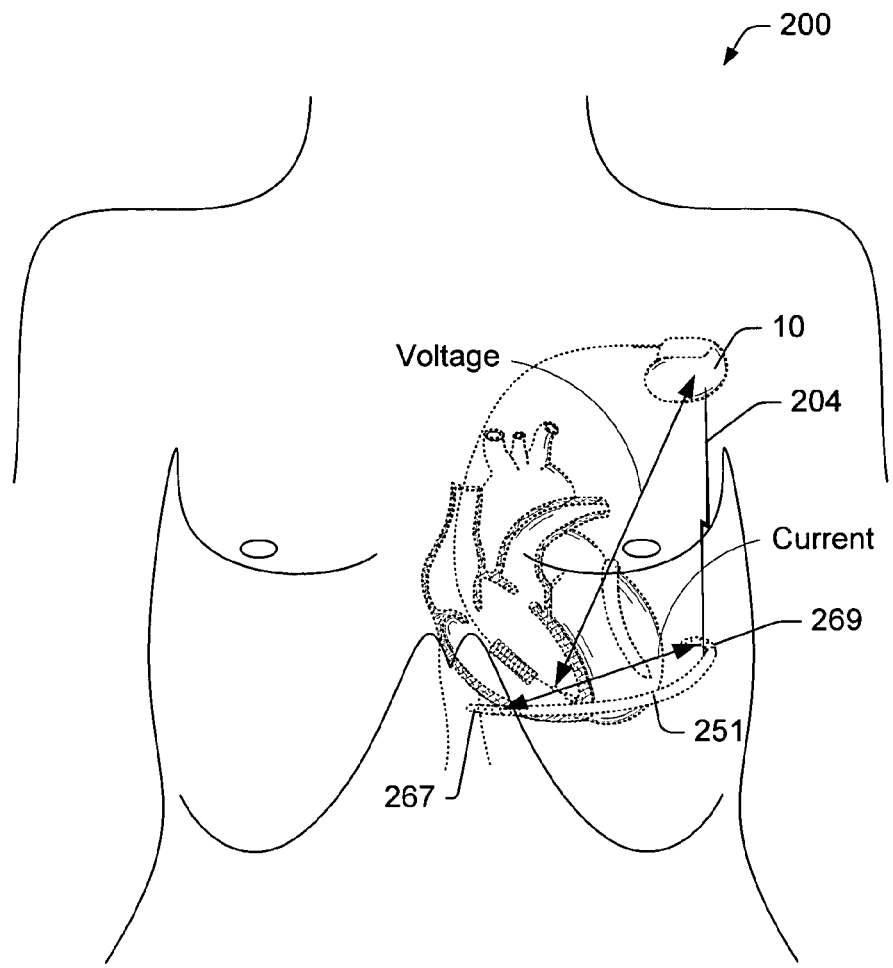
FIG. 25 is an approximate diagram of an exemplary arrangement for impedance measurement.

FIG. 25 shows an exemplary arrangement 200 that includes two implanted devices 10, 251. The heart and devices appear with dashed lines to indicate that they are subcutaneous. The exemplary device 10 includes a right ventricular lead and various electrodes (see, e.g., device 10 of FIG. 1) and the exemplary device 251 includes two electrodes 267, 269 having a spacing of about 10 cm or more. Thus, the exemplary arrangement 200 includes a pair of electrodes associated with the device 10 and a pair of electrodes associated with the device 251 that allow for introduction of current and measurement of voltage or potential.

The exemplary arrangement 200 shows an example that includes introducing a current using the two electrodes 267, 269 of the device 211 and measurement of voltage using electrodes of the device 10. The introduced current is typically an alternating current and the measured voltage typically allows for determination of a time derivative of voltage wherein the time derivative of the voltage may serve as a proxy for inter-device impedance. In this example or other examples, the current and voltage roles may be reversed for the two devices 10, 251.

An optional communication link allows unidirectional or bidirectional communication between the device 10 and the device 251. Such a communication link is optionally wireless and may conduct signals through body tissue and/or fluid. Communication between such devices may allow for coordination between current introduction and voltage measurement. Further, one device may be selected to analyze information or both devices may be selected to analyze information, for example, delivery of a defibrillation shock may not depend on current/voltage information; hence, the device 251 may have no particular need for analyzing information. In contrast, the device 10 may perform cardiac pacing through use of one or more leads such as a right ventricular lead with a ring electrode and a tip electrode. The device 10 may adjust pacing in response to current/voltage information. If the device 10 acts to measure voltage, then it may know information regarding the current provided by the device 251 or it may sense information or receive communicated information to know current characteristics relevant to impedance determinations.

The exemplary device 251 optionally includes one or more leads positionable in or near the heart and/or remote from the heart. In general, the electrodes 267, 269 typically have a relatively large surface area, for example, a surface area comparable to that of a conventional coil electrode.

An exemplary system includes two implantable devices capable of delivering cardiac therapy such as cardiac pacing therapy and cardiac defibrillation therapy. In one example, one implantable device can deliver cardiac pacing therapy while the other implantable device can deliver cardiac defibrillation therapy. One of the devices includes two electrodes having a spacing of about 10 cm or more. The two electrodes may be used to introduce a current that includes a current path across at least some myocardial tissue. In one example, the current introduced includes a current path that has end points outside of the heart such that a line between the two end points traverses at least a portion of the heart. The other device includes a proximate electrode, which may be a case of the device, and a distal electrode positioned remote from the devices, which is optionally positioned in a chamber or surface vessel of the heart. For example, a surface vessel may be selected from the coronary sinus, the great cardiac vein, etc. In this example, the two electrodes can measure a potential associated with the current introduced by the other pair of electrodes. In particular, the potential may vary over time in a manner that allows for diagnosis of cardiac condition.

An exemplary system includes two implantable devices wherein one device is capable of delivering cardiac therapy such as cardiac pacing therapy and the other device is capable of introducing a current and/or measuring potential.

An exemplary system includes two implantable devices wherein one device is capable of delivering cardiac therapy such as cardiac pacing therapy via a right ventricular lead and a left ventricular lead and the other device is capable of operating in conjunction with the cardiac therapy device for impedance determinations. In this example, the cardiac therapy device may measure potentials as a function of time wherein the potentials correspond to current introduced by the other device. The cardiac therapy device may optionally measure left ventricular potentials and right ventricular potentials that correspond to current(s) introduced by the other device. The potential information is optionally analyzed to determine characteristics of cardiac performance and, in particular, characteristics of left ventricular performance and characteristics of right ventricular performance.

An exemplary system includes two implantable devices wherein one device is capable of delivering cardiac therapy using a right atrial lead, a right ventricular lead and/or a left ventricular lead and the other device is capable of operating in conjunction with the cardiac therapy device for impedance determinations.

Figure 26:
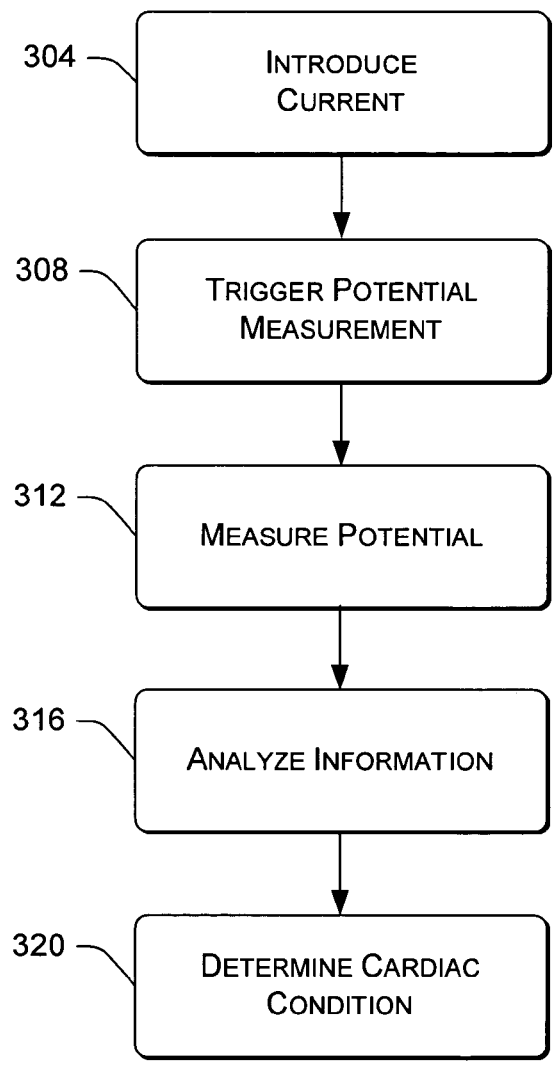
FIG. 26 is a flow diagram of an exemplary method that includes triggering a potential measurement.

FIG. 26 shows an exemplary method 300 for determining cardiac condition. In an introduction block 304, a current is introduced using a first implantable device. For example, the exemplary implantable device 251 may rely on two electrodes spaced about 10 cm or more apart to introduce a current therebetween. Prior to or during introduction of the current, a trigger block 308 triggers a second implantable device to prepare for one or more potential measurements. The trigger block 308 may operate in any of a variety of manners. For example, the second implantable device may include a circuit capable of detecting the presence of the introduced current. In another example, the first implantable device may communicate a signal receivable by the second implantable device which thereby triggers the second implantable device to perform one or more potential measurements. Current introduction and potential measurement roles of the devices may be reversed and the devices may optionally be capable of either role or both roles (e.g., consider the sensors 225, 227 of the device 211). In yet another example, the first and the second implantable devices operate with a synchronous timer and a schedule that allows for synchronous introduction of current and measurement of potential. In this particular example, one of the implantable devices may communicate a master time signal to the other device to thereby coordinate operation of the current introduction and potential measurement circuits within respective devices.

A measurement block 312 follows wherein potential measure occurs through use of the second implantable device. For example, as shown in FIG. 25, the device 10 includes a case electrode and a distal electrode capable of being used to measure potential during introduction of current by the device 251. The measurement block 316 may measure potential with respect to time as appropriate. For example, if information regarding dynamics within a cardiac cycle is desired, then the frequency of the potential measurements should be greater than 1 Hz; whereas, if information regarding enlargement of a ventricle over time is desired, then the frequency of the potential measurements may be timed to a particular event within a cardiac cycle and repeated over a period of days, weeks, etc. to help determine ventricular condition over the period of days, weeks, etc. Such an analysis may help to determine progression of congestive heart failure over time. Such an analysis may rely on determining impedance based at least partially on the potential measurements.

The exemplary method 300 continues in an analysis block 312, which may include analysis of information during measurement. In general, information may include potential measurement information, information on current introduction, information on cardiac condition, etc. A determination block 320 may rely on the analysis to determine cardiac condition. In turn, the determination may be used to commence and/or adjust cardiac therapy delivered by one or both of the implantable devices.

As described herein, various exemplary devices, methods, systems, etc., may use impedance measurements obtained by establishing or introducing an electrical current between an electrode pair and measuring the voltage or potential between another electrode pair during the current establishment. In general, mechanical activation of an associated chamber will cause a significant deflection in the resulting voltage signal or impedance. This mechanism provides a valuable tool for monitoring systolic and diastolic time intervals of the heart. For example, an impedance measurement from a chamber may be taken to indicate the mechanical activation of that chamber. For various examples, the electrode pair, 32 and 34, in the right ventricle to indicate the timing of the right ventricular contraction and the bipolar pair, 25 and 26, to indicate the timing of the left ventricular contraction. From the different times of mechanical activation, systolic and diastolic time intervals may be ascertained by comparing these times to those based on electrogram measurements. In the aforementioned example dual device example, where an implanted device includes right and left ventricular leads, measurement of potential may occur for either or both ventricles wherein the other device introduces a current. As in various other examples, current and potential roles for the devices may be reversed.

As can be seen from the foregoing, the illustrative embodiments provide a system and method for measuring a physiological parameter of, or associated with, a patient's a heart. In each of the foregoing embodiments, a current flow is established through a left side of the heart and a voltage is measured between a first location on or in the left side of the heart and a second location within the human body while establishing the current flow. This preferably includes implanting a first electrode within the coronary sinus and/or a vein of the heart, implanting a second electrode within the body, establishing a current within the body, and measuring a voltage between the first and second electrodes while establishing the current flow. As a result, impedance measurements may be obtained which provide valuable information for the patient's physician to diagnostically monitor and use which are indicative of physiological parameters of, or associated with, the heart for those patients which require cardiac rhythm management associated with the left side of the heart.

Although specific structural features and/or methodological steps have been described in connection with the illustrative embodiments, it is to be understood that the invention defined in the appended claims is not necessarily limited to the specific features or steps described.

What is claimed is:

1. An implantable system comprising:
a first pair of electrodes configured for placement internally in a patient;
a first implantable device comprising a current source operably associated with the first pair of electrodes and configured to produce a current therebetween;
a second pair of electrodes configured for placement internally in a patient;
a second implantable device comprising a voltage measuring circuit operably associated with the second pair of electrodes and configured to measure a voltage therebetween responsive to the current produced by the current source; and
logic in at least one of the first and second implantable device to determine a cardiac condition based at least in part on the current produced by the current source and the voltage measured by the voltage measuring circuit.

2. The implantable system of claim 1 wherein the first implantable device comprises an implantable cardiac defibrillation device.

3. The implantable system of claim 1 wherein the second implantable device comprises an implantable cardiac pacing device.

4. The implantable system of claim 1 wherein the logic determines at least one cardiac condition selected from a group consisting of chamber volume, cardiac output, and ventricular wall thickness.

5. The implantable system of claim 1 wherein the first pair of electrodes comprises a spacing of about 10 cm or more.

6. The implantable system of claim 1 wherein the second pair of electrodes comprises a case electrode of the second implantable device and a distal electrode positioned in the right ventricle.

7. The implantable system of claim 1 wherein the first implantable device comprises a unitary subcutaneous defibrillation device.

8. The implantable system of claim 1 wherein the second pair of electrodes comprises a right ventricular lead and a left ventricular lead.

9. The implantable system of claim 8 wherein the right ventricular lead allows for measurement of potential corresponding to current introduced by the first implantable device and wherein the left ventricular lead allows for measurement of potential corresponding to current introduced by the first implantable device.

10. The implantable system of claim 1 further comprising a communication link for communication between the first device and the second device.

* * * * *